United States Patent
Bramson et al.

(10) Patent No.: US 11,421,014 B2
(45) Date of Patent: *Aug. 23, 2022

(54) TRIFUNCTIONAL T CELL-ANTIGEN COUPLER AND METHODS AND USES THEREOF

(71) Applicant: McMaster University, Hamilton (CA)

(72) Inventors: Jonathan Bramson, Oakville (CA); Christopher W. Helsen, Oakville (CA); Galina Denisova, Hamilton (CA); Rajanish Giri, Telliarganj Allahabad (IN); Kenneth Mwawasi, Hamilton (CA)

(73) Assignee: McMaster University, Hamilton (CA)

(*) Notice: Subject to any disclaimer, the term of this patent is extended or adjusted under 35 U.S.C. 154(b) by 268 days.

This patent is subject to a terminal disclaimer.

(21) Appl. No.: 16/547,421

(22) Filed: Aug. 21, 2019

(65) Prior Publication Data

US 2020/0071377 A1  Mar. 5, 2020

Related U.S. Application Data

(63) Continuation of application No. 15/117,173, filed as application No. PCT/CA2015/000068 on Feb. 6, 2015, now Pat. No. 10,435,453.

(Continued)

(51) Int. Cl.
*C07K 14/73* (2006.01)
*C07K 16/28* (2006.01)
(Continued)

(52) U.S. Cl.
CPC ........ *C07K 14/70514* (2013.01); *A61K 35/17* (2013.01); *C07K 14/7051* (2013.01); *C07K 16/2809* (2013.01); *C07K 16/32* (2013.01); *C07K 2317/31* (2013.01); *C07K 2317/622* (2013.01); *C07K 2317/73* (2013.01);
(Continued)

(58) Field of Classification Search
None
See application file for complete search history.

(56) References Cited

U.S. PATENT DOCUMENTS

| 7,083,785 B2 | 8/2006 | Browning et al. |
| 7,947,805 B2 | 5/2011 | Belloir et al. |

(Continued)

FOREIGN PATENT DOCUMENTS

| WO | WO-9957268 A1 | 11/1999 |
| WO | WO-2004106380 A2 | 12/2004 |

(Continued)

OTHER PUBLICATIONS

Apuri, S., et al., "Outcomes in Patients with Acute Myeloid Leukemia Preceded by Breast Cancer", Blood, 120(21): 4316 (2012).

(Continued)

*Primary Examiner* — Arthur S Leonard
(74) *Attorney, Agent, or Firm* — Goodwin Procter LLP

(57) ABSTRACT

A trifunctional molecule comprising a target-specific ligand, a ligand that binds a protein associated with the TCR complex and a T cell receptor signaling domain polypeptide is provided. Engineering T cells with this novel receptor engenders antigen specific activation of numerous T cell functions, including cytokine production, degranulation and cytolysis.

9 Claims, 20 Drawing Sheets

Specification includes a Sequence Listing.

Related U.S. Application Data

(60) Provisional application No. 61/936,906, filed on Feb. 7, 2014.

(51) Int. Cl.
*C07K 14/725* (2006.01)
*C07K 16/32* (2006.01)
*A61K 35/17* (2015.01)

(52) U.S. Cl.
CPC ...... *C07K 2318/20* (2013.01); *C07K 2319/00* (2013.01); *C07K 2319/03* (2013.01)

(56) References Cited

U.S. PATENT DOCUMENTS

| | | |
|---|---|---|
| 8,084,030 B2 | 12/2011 | Kalled et al. |
| 9,718,893 B2 | 8/2017 | Jung et al. |
| 10,435,453 B2 | 10/2019 | Bramson et al. |
| 10,640,562 B2 | 5/2020 | Bramson et al. |
| 10,822,408 B2 | 11/2020 | Hamburger et al. |
| 11,001,621 B1 | 5/2021 | Bramson et al. |
| 11,008,376 B2 | 5/2021 | Bramson et al. |
| 11,110,123 B2 | 9/2021 | Bramson et al. |
| 11,111,298 B2 | 9/2021 | Bramson et al. |
| 11,198,737 B2 | 12/2021 | Helsen et al. |
| 2002/0081296 A1 | 6/2002 | Theill et al. |
| 2002/0107869 A1 | 8/2002 | Leroy |
| 2003/0012783 A1 | 1/2003 | Kindsvogel |
| 2003/0095967 A1 | 5/2003 | MacKay et al. |
| 2004/0162411 A1 | 8/2004 | Lanzavecchia |
| 2006/0233791 A1 | 10/2006 | Tedder et al. |
| 2007/0048221 A1 | 3/2007 | Kindsvogel |
| 2007/0048319 A1 | 3/2007 | Kindsvogel |
| 2007/0049735 A1 | 3/2007 | Kindsvogel |
| 2008/0044413 A1 | 2/2008 | Hammond et al. |
| 2008/0095766 A1 | 4/2008 | Koenig et al. |
| 2008/0260737 A1 | 10/2008 | Ponce et al. |
| 2008/0267965 A1 | 10/2008 | Kalled et al. |
| 2012/0082661 A1 | 4/2012 | Kalled et al. |
| 2012/0213768 A1 | 8/2012 | Oh et al. |
| 2013/0101599 A1 | 4/2013 | Borges et al. |
| 2013/0156770 A1 | 6/2013 | Kufer et al. |
| 2013/0273055 A1 | 10/2013 | Borges et al. |
| 2013/0280280 A1 | 10/2013 | Algate et al. |
| 2013/0330323 A1 | 12/2013 | Dunn et al. |
| 2015/0119555 A1 | 4/2015 | Jung et al. |
| 2015/0322169 A1 | 11/2015 | June et al. |
| 2016/0228546 A1 | 8/2016 | Stagliano et al. |
| 2016/0362472 A1 | 12/2016 | Bitter et al. |
| 2016/0368964 A1 | 12/2016 | Bramson et al. |
| 2019/0153115 A1 | 5/2019 | Schellenberger et al. |
| 2020/0024345 A1 | 1/2020 | Bramson et al. |
| 2020/0071377 A1 | 3/2020 | Bramson et al. |
| 2020/0239571 A1 | 7/2020 | Bramson et al. |
| 2020/0261500 A1 | 8/2020 | Bramson et al. |
| 2020/0270330 A1 | 8/2020 | Bramson et al. |
| 2020/0308278 A1 | 10/2020 | Bramson et al. |
| 2020/0392247 A1 | 12/2020 | Helsen et al. |
| 2021/0369780 A1 | 12/2021 | Bramson et al. |

FOREIGN PATENT DOCUMENTS

| | | |
|---|---|---|
| WO | WO-2005040220 A1 | 5/2005 |
| WO | WO-2010037835 A2 | 4/2010 |
| WO | WO-2012066058 A1 | 5/2012 |
| WO | WO-2012163805 A1 | 12/2012 |
| WO | WO-2013092001 A1 | 6/2013 |
| WO | WO-2013123061 A1 | 8/2013 |
| WO | WO-2013132268 A1 | 9/2013 |
| WO | WO-2014011988 A2 | 1/2014 |
| WO | WO-2014122144 A1 | 8/2014 |
| WO | WO-2015006749 A2 | 1/2015 |
| WO | WO-2015117229 A1 | 8/2015 |
| WO | WO-2016166139 A1 | 10/2016 |
| WO | WO-2017040344 A2 | 3/2017 |
| WO | WO-2017087723 A1 | 5/2017 |
| WO | WO-2018121605 A1 | 7/2018 |
| WO | WO-2019071358 A1 | 4/2019 |
| WO | WO-2020018727 A1 | 1/2020 |

OTHER PUBLICATIONS

EP15746948.7 Communication pursuant to Rule 114(2) EPC dated Jan. 21, 2019.
Geyer et al. Review: Current clinical applications of chimeric antigen receptor (CAR) modified T cells. Cytotherapy 18(11):1393-1409 (2016).
Jamal, S., et al., "Immunophenotypic Analysis of Peripheral T-Cell Neoplasms", Am. J. Clin. Pathol., vol. 116, pp. 512-526, (2001).
Kiewe, P., et al., "Phase I Trial of the Trifunctional Anti-HER2 x Anti-CD3 Antibody Ertumaxomab in Matastatic Breast Cancer", Clin. Cancer Res., 12(10), pp. 3085-3091, (2006).
Kimchi-Sarfaty, C., et al., "A 'silent' polymorphiosm in the MDR1 gene changes substrate specificity", Science, 315:525-528, (2007).
Klinger et al. Harnessing T cells to fight cancer with BiTE® antibody constructs—past developments and future directions. Immunol Rev. 270(1):193-208 (2016).
Löffler et al. A recombinant bispecific single-chain antibody, CD19 X CD3, induces rapid and high lymphoma-directed cytotoxicity by unstimulated T lymphocytes. Blood 95(6):2098-2103 (2000).
Popik, et al. CD4 receptor localized to non-raft membrane microdomains supports HIV-1 entry. Identification of a novel raft localization marker in CD4. J Biol Chem 279(1):704-712 (2004).
Rosenberg, et al. Use of tumor-infiltrating lymphocytes and interleukin-2 in the immunotherapy of patients with matastatic melanoma. A preliminary report. NEJM 319: 1676 (1988).
U.S. Appl. No. 17/301,884, filed Apr. 16, 2021.
U.S. Appl. No. 15/929,510 Office Action dated Nov. 9, 2020.
U.S. Appl. No. 15/929,513 Office Action dated May 11, 2021.
U.S. Appl. No. 15/929,513 Office Action dated Nov. 30, 2020.
U.S. Appl. No. 16/904,451 Office Action dated Dec. 1, 2020.
U.S. Appl. No. 16/904,451 Office Action dated May 10, 2021.
U.S. Appl. No. 17/248,174 Office Action dated Mar. 11, 2021.
Voet, D., et. al., Biochemistry, John Wiley and Sons, New York, pp. 126-128, (1990).
Wykosky, J., et al. The EphA2 repector and ephrinA1 ligand in solid tumors: function and therapeutic targeting, Mol Cancer Res, 6(12):1795-1806 (2008).
Zhukovsky et al. Bispecific antibodies and CARs: generalized immunotherapeutics harnessing T cell redirection. Curr Opin Immunol 40:24-35 (2016).
Acuto et al. T cell activation and the cytoskeleton. Annu. Rev. Immunol. 18:165-184 (2000).
Alabanza et al. Function of Novel Anti-CD19 Chimeric Antigen Receptors with Human Variable Regions Is Affected by Hinge and Transmembrane Domains. Mol Ther 25(11):2452-2465 (2017).
Anderson et al. Comodulation of CD3 and CD4. Evidence for a specific association between CD4 and approximately 5% of the CD3:T cell receptor complexes on helper T lymphocytes. J Immunol 140:1732-1737 (1988).
Arcaro et al. Essential role of CD8 palmitoylation in CD8 coreceptor function. J. Immunol. 165:2068-2076 (2000).
Chames et al. Bispecific antibodies for cancer therapy: the light at the end of the tunnel? MAbs 1:539-547 (2009).
Chervin et al. The impact of TCR-binding properties and antigen presentation format on T cell responsiveness. J. Immunol. 183:1166-1178 (2009).
Compte et al. Inhibition of tumor growth in vivo by in situ secretion of bispecific anti-CEA x anti-CD3 diabodies from lentivirally transduced human lymphocytes. Cancer Gene Therapy 14:380-388 (2007).
Deans et al. Interaction of CD4:lck with the T cell receptor/CD3 complex induces early signaling events in the absence of CD45 tyrosine phosphatase. Eur J Immunol 22:661-668 (1992).

(56) References Cited

OTHER PUBLICATIONS

Dotti et al. Fifteen years of gene therapy based on chimeric antigen receptors: "are we nearly there yet?" Hum. Gene Ther. 20:1229-1239 (2009).
Finney et al. Activation of resting human primary T cells with chimeric receptors: costimulation from CD28, inducible costimulator, CD134, and CD137 in series with signals from the TCR zeta chain. J. Immunol. 172:104-113 (2004).
Fournier et al. Bispecific antibodies and trispecific immunocytokines for targeting the immune system against cancer: preparing for the future. BioDrugs 27:35-53 (2013).
Fragoso et al. Lipid raft distribution of CD4 depends on its palmitoylation and association with Lck, and evidence for CD4-induced lipid raft aggregation as an additional mechanism to enhance CD3 signaling. J. Immunol. 170:913-921 (2003).
Frankel et al. Targeting T cells to tumor cells using bispecific antibodies. Curr Opin Chem Biol 17(3):385-392 (2013).
Fry et al. T-cell adoptive immunotherapy for acute lymphoblastic leukemia. Hematology Am. Soc. Hematol. Educ. Program 2013:348-353 (2013).
Geiger et al. Integrated src kinase and costimulatory activity enhances signal transduction through single-chain chimeric receptors in T lymphocytes. Blood 98(8):2364-2371 (2001).
Hammond et al. Selective targeting and potent control of tumor growth using an EphA2/CD3-Bispecific single-chain antibody construct. 67(8):3927-3935 (2007).
Han et al. Chimeric antigen receptor-engineered T cells for cancer immunotherapy: progress and challenges. J. Hematol. Oncol. 6:47 (2013).
He et al. T-cell antigen receptor triggering and lipid rafts: a matter of space and time scales. Talking Point on the involvement of lipid rafts in T-cell activation. EMBO Rep. 9:525-530 (2008).
Helsen et al. The chimeric TAC receptor co-opts the T cell receptor yielding robust anti-tumor activity without toxicity. Nature Communications 9:3049 (2018).
Helsen et al. Tri-functional T cell receptor antigen coupler (Tri-TAC): a novel methodto direct T cells against tumors. J Immunother Cancer 2(Supp 3):p. 17 (2014).
Hexham et al. Optimization of the anti-(human CD3) immunotoxin DT389-scFv(UCHT1) N-terminal sequence to yield a homogeneous protein. Biotechnol Appl Biochem 34(Pt 3):183-187 (2010).
Humphries. Adoptive cell therapy: Honing that killer instinct. Nature 504:S13-15 (2013).
Itano et al. The cytoplasmic domain of CD4 promotes the development of CD4 lineage T cells. J Exp Med. 183(3):731-741 (1996).
Kim et al. A zinc clasp structure tethers Lck to T cell coreceptors CD4 and CD8. Science 301:1725-1728 (2003).
Kochenderfer et al. Treating B-cell cancer with T cells expressing anti-CD19 chimeric antigen receptors. Nat. Rev. Clin. Oncol. 10:267-276 (2013).
Kuhns et al. TCR Signaling Emerges from the Sum of Many Parts. Front. Immunol. 3:159 (2012).
Methi et al. Short-interfering RNA-mediated Lck knockdown results in augmented downstream T cell responses. J. Immunol. 175(11):7398-7406 (2005).
Milone et al. Chimeric receptors containing CD137 signal transduction domains mediate enhanced survival of T cells and increased antileukemic efficacy in vivo. Mol. Ther. 17:1453-1464 (2009).
Molhoj, et al. CD19-/CD3-bispecific antibody of the BiTE class is far superior to tandem diabody with respect to redirected tumor cell lysis. Mol Immunol. Mar. 2007;44(8):1935-43. Epub Nov. 2, 2006.
Nagorsen et al. Immunomodulatory therapy of cancer with T cell-engaging BiTE antibody blinatumomab. Exp Cell Res 317(9):1255-1260 (2011).
Nagorsen et al. Immunotherapy of lymphoma and leukemia with T-cell engaging BiTE antibody blinatumomab. Leuk Lymph 50(6):886-891 (2009).
Panka et al. Variable region framework differences result in decreased or increased affinity of variant anti-digoxin antibodies. PNAS USA 85:3080-3084 (1988).

PCT/CA2015/000068 International Preliminary Report on Patentability dated Aug. 18, 2016.
PCT/CA2015/000068 International Search Report and Written Opinion dated May 4, 2015.
PCT/CA2018/051290 International Search Report and Written Opinion dated Jan. 17, 2019.
PCT/US2019/042297 International Search Report and Written Opinion dated Oct. 30, 2019.
Pilozzi et al. Co-expression of CD79a (JCB117) and CD3 by lymphoblastic lymphoma. J Pathol 186(2):140-143. (1998).
Portell et al. Clinical and pharmacologic aspects of blinatumomab in the treatment of B-cell acute lymphoblastic leukemia. Clin. Pharmacol. 5(Suppl 1):5-11 (2013).
Rudikoff et al. Single amino acid substitution altering antigen-binding specificity. PNAS USA 79:1979-1983 (1982).
Thompson et al. CLUSTAL W: improving the sensitivity of progressive multiple sequence alignment through sequence weighting, position-specific gap penalties and weight matrix choice. Nucleic Acid Res. 22:4673-4680 (1994).
Till et al. CD20-specific adoptive immunotherapy for lymphoma using a chimeric antigen receptor with both CD28 and 4-1BB domains: pilot clinical trial results. Blood 119(17):3940-3950 (2012).
U.S. Appl. No. 15/117,173 Office Action dated Jan. 24, 2018.
U.S. Appl. No. 15/117,173 Office Action dated Jun. 21, 2019.
U.S. Appl. No. 15/117,173 Office Action dated Oct. 24, 2018.
U.S. Appl. No. 16/442,274 Office Action dated Nov. 6, 2019.
Velasquez. T cells expressing CD19-specific Engager Molecules for the Immunotherapy of CD19-positive Malignancies. Sci Rep 6:27130 (2016).
Wels et al. Construction, Bacterial Expression and Characterization of a Bifunctional Single-Chain Antibody-Phosphatase Fusion Protein Targeted to the human ERBB-2 receptor. Nature Biotech 10:1128-1132 (1992).
Wittlich et al. Structural characterization of the transmembrane and cytoplasmic domains of human CD4. Biochimica et Biophysica Acta 1768:2949-2960 (2007).
Yin et al. Crystal structure of a complete ternary complex of T-cell receptor, peptide-MHC, and CD4. PNAS USA 109:5405-5410 (2012).
Zahnd et al. Efficient Tumor Targeting with High-Affinity Designed Ankyrin Repeat Proteins: Effects of Affinity and Molecular Size. Cancer Res 70:1595-1605 (2010).
Zahnd et al. Selection and Characterization of Her2 Binding-designed Ankyrin Repeat Proteins. The Journal Of Biological Chemistry 281(46):35167-35175 (2006).
Zhang et al. Sequestration of CD4-associated Lck from the TCR complex may elicit T cell hyporesponsiveness in nonobese diabetic mice. J Immunol 160:1148-1157 (1998).
Carpenter, R.O., et al., B-cell maturation antigen is a promising target for adoptive T-cell therapy of multiple myeloma, Clin Cancer Res, 19(8): 2048-2060 (2013).
Chiu, A., et al., Hodgkin lymphoma cells express TACI and BCMA receptors and generate survival and proliferation signals in response to BAFF and APRIL, Blood, 109(2): 729-739 (2007).
De Novo, New Products from R&D Systems, Antibody catalog including BCMA mAB, pp. 1-10 (Mar. 2004).
Deng, S., et al., B-lymphocyte-induced maturation protein1 up-regulates the expression of B-cell maturation antigen in mouse plasma cells, Mol Biol Rep, 37(8): 3747-3755 (2010).
Deshayes, S., et al., Cell-penetrating peptides: tools for intracellular delivery of therapeutics, Cell Mol Life Sci, 62(16): 1839-1849 (2005).
Guadagnoli, M., et al., Development and characterization of APRIL antagonistic monoclonal antibodies for treatment of B-cell lymphomas, Blood, 117(25): 6856-6865 (2011).
Marsden, H.R., et al., Model systems for membrane fusion, Chem Soc Rev, 40(3): 1572-1585 (2011).
Novak, A.J., et al., Expression of BLyS and its receptors in B-cell non-Hodgkin lymphoma: correlation with disease activity and patient outcome, Blood, 104(8): 2247-2253 (2004).
Ryan, M.C., et al., Antibody targeting of B-cell maturation antigen on malignant plasma cells, Mol Cancer Ther, 6(11): 3009-3018 (2007).

(56) References Cited

OTHER PUBLICATIONS

Tai, Y-T., et al., Novel Fc-Engineered Anti-B Cell Maturation Antigen-Monomethyl Auristatin F Antibody-Drug Conjugate (GSK2857916) Induces Potent and Selective Anti-Multiple Myeloma Activity Via Enhanced Effector Function and Direct Tumor Cell Killing, Blood, 122(21): 877 (2013).
U.S. Appl. No. 17/304,924 Application filed Jun. 28, 2021.
U.S. Appl. No. 17/394,280 Application filed Aug. 4, 2021.
U.S. Appl. No. 17/394,280 Office Action dated Dec. 10, 2021.
Wang, M., et al., Efficient delivery of genome-editing proteins using bioreducible lipid nanoparticles, PNAS, 113(11): 2868-2873 (2016).
Yong, K. L., et al., Evaluation Of Bcma As a Therapeutic Target In Multiple Myeloma Using An Antibody-Drug Conjugate, Blood, 122(21): 4447 (2013).

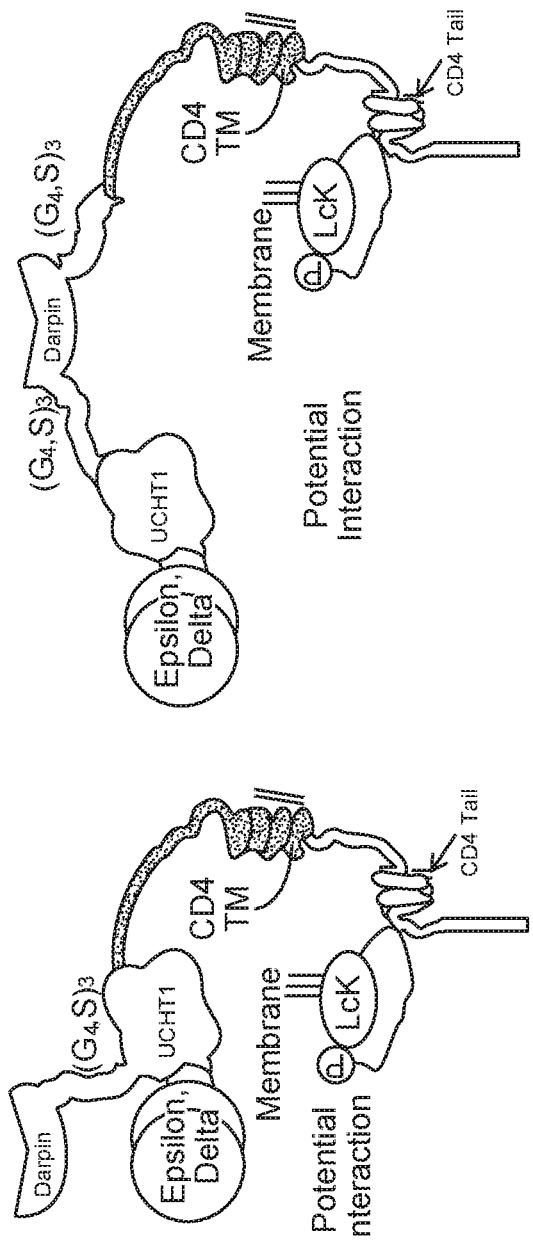
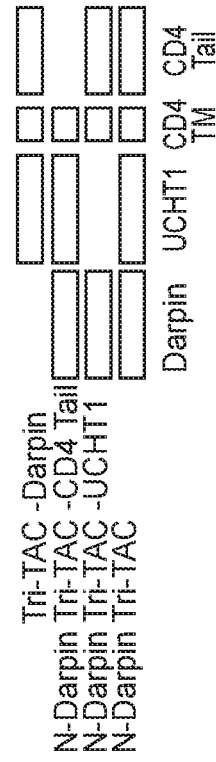
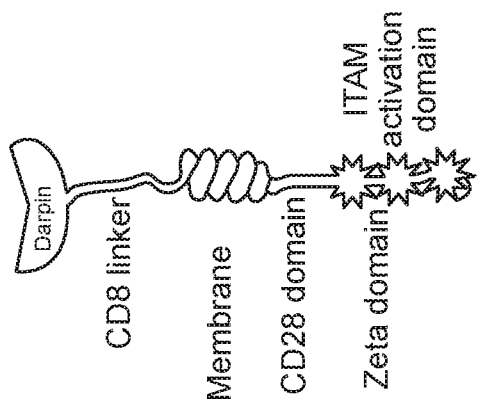
FIG. 1A
FIG. 1B
FIG. 1C
FIG. 1D

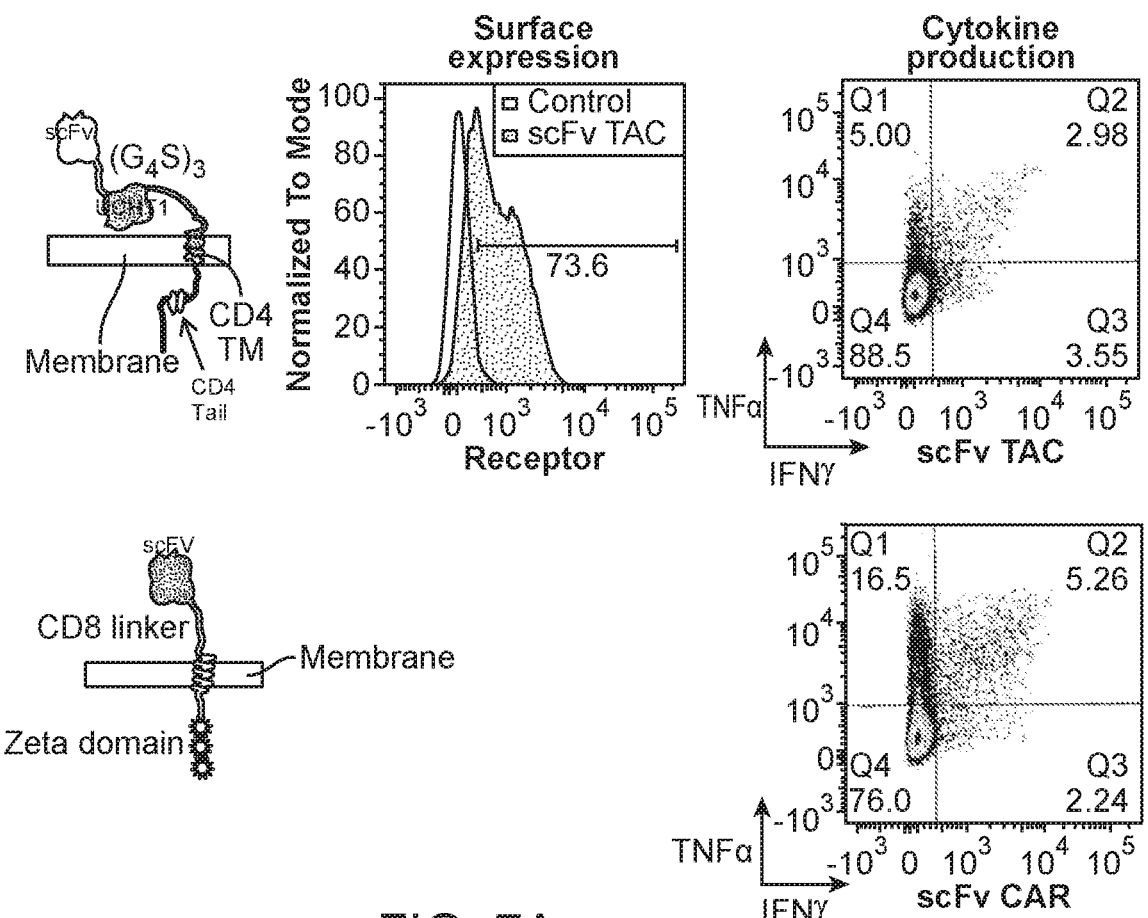
FIG. 7A
FIG. 7B
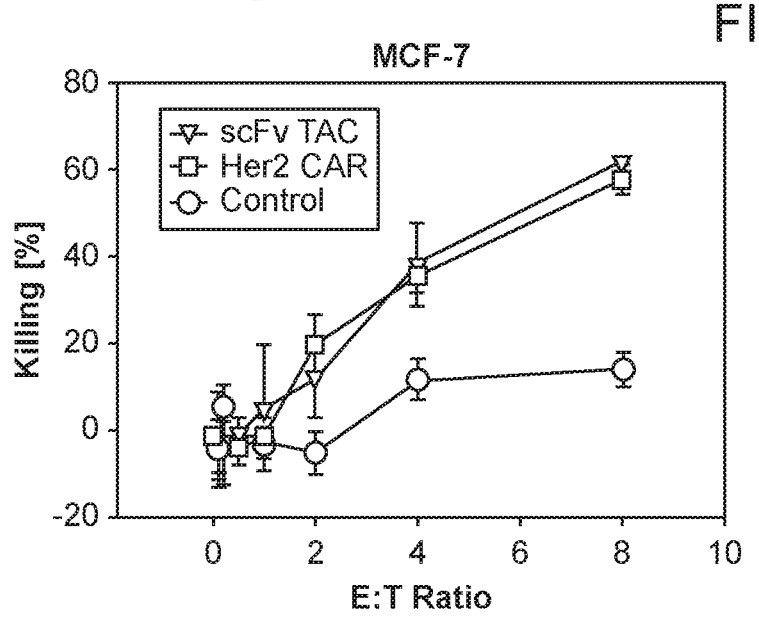
FIG. 7C

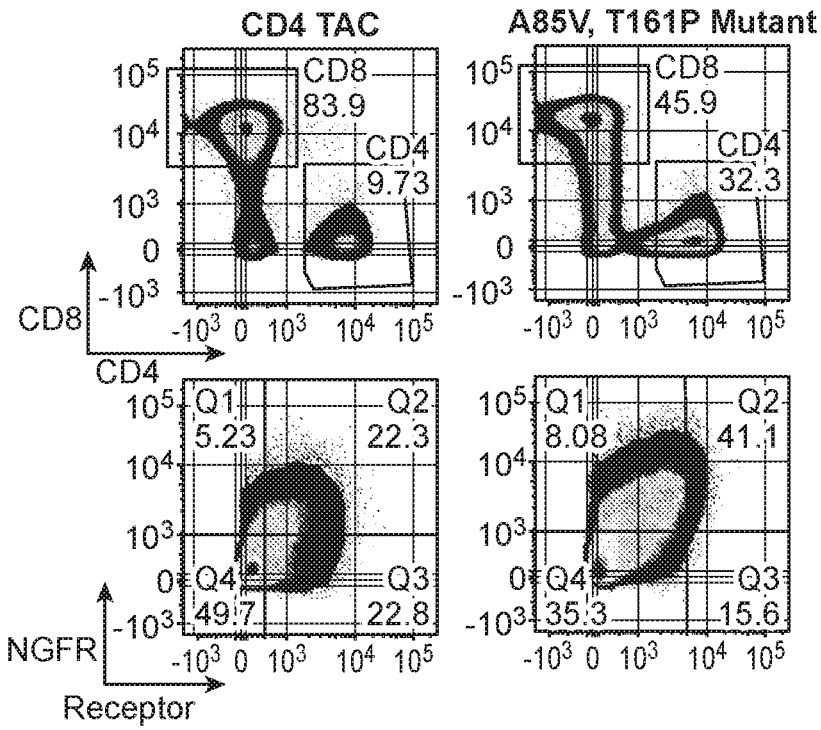
FIG. 16A
FIG. 16B
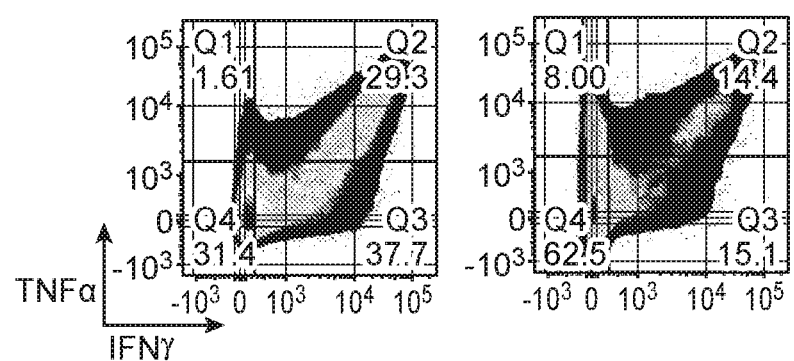
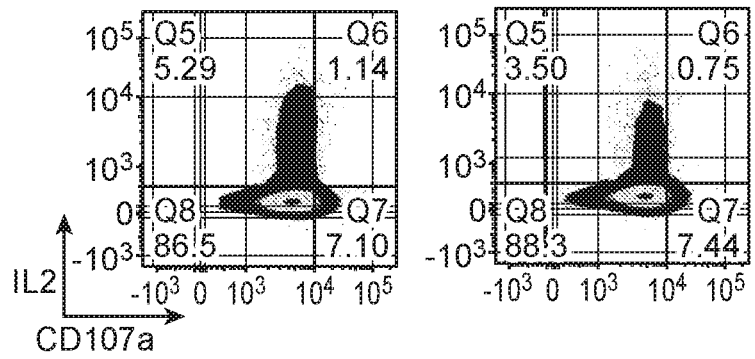
FIG. 16C

```
SEQUENCE LISTING

<160> NUMBER OF SEQ ID NOS: 25

<210> SEQ ID NO 1
<211> LENGTH: 1575
<212> TYPE: DNA
<213> ORGANISM: Artificial Sequence
<220> FEATURE:
<223> OTHER INFORMATION: Synthetic

<400> SEQUENCE: 1
atggatttcc aggtccagat tttctccttc ctgctgattt ccgcaagcgt cattatgtca      60
cggggctccg acctgggcaa aaagctgctg gaggccgcta gggccgggca ggacgatgaa     120
gtgagaatcc tgatggccaa cggggctgac gtgaatgcta aggatgagta cggcctgacc     180
cccctgtatc tggctacagc acacggccat ctggagatcg tggaagtcct gctgaaaaac     240
ggagccgacg tgaatgcagt cgatgccatt gggttcactc ctctgcacct ggcagccttt     300
```

```
atcggacatc tggagattgc agaagtgctg ctgaagcacg gcgctgacgt gaacgcacag    360
gataagttcg gaaaaaccgc ttttgacatc agcattggca acggaaatga agacctggct    420
gaaatcctgc agaaactgaa tgaacagaaa ctgattagcg aagaagacct gaaccccggg    480
ggaggaggag ggagcggggg aggaggcagc ggcggggggag gctctggagg aggagggagc    540
ggatccatgg acatccagat gactcagacc acaagctccc tgtctgcaag tctgggcgac    600
cgggtgacaa tctcctgcag agcctctcag gatattagga actacctgaa ttggtatcag    660
cagaaacctg atggcacagt caagctgctg atctactata ccagccggct gcactcaggc    720
gtgccaagca aattctcagg aagcggctcc gggactgact actccctgac catctctaac    780
ctggagcagg aagatattgc tacctatttc tgccagcagg caatacact gccctggact     840 tttgccggag gcaccaaact ggagatcaag gggggaggcg ggagtggagg cggggatca    900 ggaggaggag gcagcggagg aggagggtcc gaggtccagc tgcagcagag cggaccagaa    960
ctggtgaagc ccggagcaag tatgaaaatc tcctgtaagg cctcaggata cagcttcacc   1020
ggctatacaa tgaactgggt gaaacagtcc catggcaaga acctggaatg gatggggctg   1080
attaatcctt acaaaggcgt cagcacctat aatcagaagt ttaaagacaa ggccacactg   1140
actgtggata agtctagttc aaccgcttac atggagctgc tgtccctgac atctgaagac   1200
agtgccgtgt actattgtgc tcggtctggc tactatgggg acagtgattg gtacttcgat   1260
gtctggggac agggcactac cctgaccgtg ttttctacta gtggcggagg aggatcactc   1320
gagagcggac aggtgctgct ggaatccaat atcaaagtcc tgcccacttg gtctacccc    1380 gtgcagccta tggctctgat tgtgctggga ggagtcgcag gactgctgct gtttatcggg   1440
ctgggaattt tcttttgcgt gcgctgccgg caccggagaa ggcaggccga gcgcatgagc   1500
cagatcaagc gactgctgag cgagaagaaa acctgtcagt gtccccatag attccagaag   1560
acctgttcac ccatt                                                     1575
```

<210> SEQ ID NO 2  
<211> LENGTH: 525  
<212> TYPE: PRT  
<213> ORGANISM: Artificial Sequence  
<220> FEATURE:  
<223> OTHER INFORMATION: Synthetic

<400> SEQUENCE: 2

```
Met Asp Phe Gln Val Gln Ile Phe Ser Phe Leu Leu Ile Ser Ala Ser
1               5                   10                  15

Val Ile Met Ser Arg Gly Ser Asp Leu Gly Lys Lys Leu Leu Glu Ala
            20                  25                  30

Ala Arg Ala Gly Gln Asp Asp Glu Val Arg Ile Leu Met Ala Asn Gly
        35                  40                  45

Ala Asp Val Asn Ala Lys Asp Glu Tyr Gly Leu Thr Pro Leu Tyr Leu
    50                  55                  60

Ala Thr Ala His Gly His Leu Glu Ile Val Glu Val Leu Leu Lys Asn
65                  70                  75                  80

Gly Ala Asp Val Asn Ala Val Asp Ala Ile Gly Phe Thr Pro Leu His
                85                  90                  95

Leu Ala Ala Phe Ile Gly His Leu Glu Ile Ala Glu Val Leu Leu Lys
            100                 105                 110

His Gly Ala Asp Val Asn Ala Gln Asp Lys Phe Gly Lys Thr Ala Phe
        115                 120                 125
```

```
Asp Ile Ser Ile Gly Asn Gly Asn Glu Asp Leu Ala Glu Ile Leu Gln
            130                 135                 140

Lys Leu Asn Glu Gln Lys Leu Ile Ser Glu Glu Asp Leu Asn Pro Gly
145                 150                 155                 160

Gly Gly Gly Gly Ser Gly Gly Gly Ser Gly Gly Gly Gly Ser Gly
                165                 170                 175

Gly Gly Gly Ser Gly Ser Met Asp Ile Gln Met Thr Gln Thr Thr Ser
                180                 185                 190

Ser Leu Ser Ala Ser Leu Gly Asp Arg Val Thr Ile Ser Cys Arg Ala
                195                 200                 205

Ser Gln Asp Ile Arg Asn Tyr Leu Asn Trp Tyr Gln Gln Lys Pro Asp
            210                 215                 220

Gly Thr Val Lys Leu Leu Ile Tyr Tyr Thr Ser Arg Leu His Ser Gly
225                 230                 235                 240

Val Pro Ser Lys Phe Ser Gly Ser Gly Ser Gly Thr Asp Tyr Ser Leu
                245                 250                 255

Thr Ile Ser Asn Leu Glu Gln Glu Asp Ile Ala Thr Tyr Phe Cys Gln
            260                 265                 270

Gln Gly Asn Thr Leu Pro Trp Thr Phe Ala Gly Gly Thr Lys Leu Glu
            275                 280                 285

Ile Lys Gly Gly Gly Gly Ser Gly Gly Gly Gly Ser Gly Gly Gly Gly
290                 295                 300

Ser Gly Gly Gly Gly Ser Glu Val Gln Leu Gln Gln Ser Gly Pro Glu
305                 310                 315                 320

Leu Val Lys Pro Gly Ala Ser Met Lys Ile Ser Cys Lys Ala Ser Gly
                325                 330                 335

Tyr Ser Phe Thr Gly Tyr Thr Met Asn Trp Val Lys Gln Ser His Gly
                340                 345                 350

Lys Asn Leu Glu Trp Met Gly Leu Ile Asn Pro Tyr Lys Gly Val Ser
            355                 360                 365

Thr Tyr Asn Gln Lys Phe Lys Asp Lys Ala Thr Leu Thr Val Asp Lys
370                 375                 380

Ser Ser Ser Thr Ala Tyr Met Glu Leu Leu Ser Leu Thr Ser Glu Asp
385                 390                 395                 400

Ser Ala Val Tyr Tyr Cys Ala Arg Ser Gly Tyr Tyr Gly Asp Ser Asp
                405                 410                 415

Trp Tyr Phe Asp Val Trp Gly Gln Gly Thr Thr Leu Thr Val Phe Ser
            420                 425                 430

Thr Ser Gly Gly Gly Gly Ser Leu Glu Ser Gly Gln Val Leu Leu Glu
            435                 440                 445

Ser Asn Ile Lys Val Leu Pro Thr Trp Ser Thr Pro Val Gln Pro Met
450                 455                 460

Ala Leu Ile Val Leu Gly Gly Val Ala Gly Leu Leu Leu Phe Ile Gly
465                 470                 475                 480

Leu Gly Ile Phe Phe Cys Val Arg Cys Arg His Arg Arg Gln Ala
                485                 490                 495

Glu Arg Met Ser Gln Ile Lys Arg Leu Leu Ser Glu Lys Lys Thr Cys
                500                 505                 510

Gln Cys Pro His Arg Phe Gln Lys Thr Cys Ser Pro Ile
                515                 520                 525

<210> SEQ ID NO 3
<211> LENGTH: 1647
<212> TYPE: DNA
```

<213> ORGANISM: Artificial Sequence
<220> FEATURE:
<223> OTHER INFORMATION: Synthetic

<400> SEQUENCE: 3

```
atggactttc aggtgcagat tttctctttt ctgctgattt ccgcaagcgt catcgagctc      60
ggggggggggg ggtcaggatc catggacatc cagatgactc agaccacaag ctccctgagc    120
gcatccctgg cgaccgagt gacaatctca tgcagagcca gccaggatat taggaactac     180
ctgaattggt atcagcagaa acctgacggc acagtcaagc tgctgatcta ctatacttcc    240
cggctgcact ctggcgtgcc aagtaaattc tctgggagtg gatcaggcac tgactactca    300
ctgaccatca gcaacctgga gcaggaagat attgctacct atttctgcca gcagggcaat    360
acactgccct ggactttgc aggcgggacc aaactggaga tcaagggcgg cggcggaagt     420
ggaggaggag gctcaggcgg aggagggagc ggcggaggag gcagcgaggt ccagctgcag    480
cagagcggac cagaactggt gaagcctggc gcatccatga aatctcttg taaggcctct     540
gggtacagtt tcaccggata caatgaac tgggtgaaaa agtctcatgg caagaacctg      600
gaatggatgg gctgattaa tccttacaaa ggcgtcagca cctataatca gaagtttaaa     660
gacaaggcca cactgactgt ggataagtct agttcaaccg cttacatgga gctgctgtca    720
ctgacaagcg aagactccgc cgtgtactat tgcgctagga gcggatacta tggcgactcc    780
gattggtact cgatgtctg ggggcaggga actaccctga ccgtgtttag cactagtgga    840
ggaggaggct ctggaggagg agggagtgga ggcggggat caggaggagg aggcagcgat    900
atcatgtcac ggggctccga cctgggcaaa aagctgctgg aggccgctag gccgggcag    960
gacgatgaag tgagaatcct gatggccaac ggggctgacg tgaatgctaa ggatgagtac   1020
ggcctgaccc ccctgtatct ggctacagca cacggccatc tggagatcgt ggaagtcctg   1080
ctgaaaaacg gagccgacgt gaatgcagtc gatgccattg ggttcactcc tctgcacctg   1140
gcagccttta tcggacatct ggagattgca gaagtgctgc tgaagcacgg cgctgacgtg   1200
aacgcacagg ataagttcgg aaaaaccgct tttgacatca gcattggcaa cggaaatgaa   1260
gacctggctg aaatcctgca gaaactgaat gaacagaaac tgattagcga agaagacctg   1320
aacgtcgacg gaggaggagg gtctggagga ggggaagtg gcgggggagg cagcggggga   1380
ggcgggtctc tcgagagtgg ccaggtgctc tggaaagca atatcaaggt cctgccaact   1440
tggtccaccc cagtgcagcc tatggctctg attgtgctgg gaggagtcgc aggactgctg   1500
ctgtttatcg gcctggggat tttcttttgc gtgcgctgcc ggcaccggag aaggcaggct   1560
gagcgcatgt ctcagattaa gcgactgctg agcgagaaga gacctgtca gtgccccat    1620
agattccaga aaacctgttc acccatt                                       1647
```

<210> SEQ ID NO 4
<211> LENGTH: 549
<212> TYPE: PRT
<213> ORGANISM: Artificial Sequence
<220> FEATURE:
<223> OTHER INFORMATION: Synthetic

<400> SEQUENCE: 4

Met Asp Phe Gln Val Gln Ile Phe Ser Phe Leu Leu Ile Ser Ala Ser
1               5                   10                  15

Val Ile Glu Leu Gly Gly Gly Gly Ser Gly Ser Met Asp Ile Gln Met
            20                  25                  30

Thr Gln Thr Thr Ser Ser Leu Ser Ala Ser Leu Gly Asp Arg Val Thr

```
                35                  40                  45
Ile Ser Cys Arg Ala Ser Gln Asp Ile Arg Asn Tyr Leu Asn Trp Tyr
 50                  55                  60

Gln Gln Lys Pro Asp Gly Thr Val Lys Leu Leu Ile Tyr Tyr Thr Ser
 65                  70                  75                  80

Arg Leu His Ser Gly Val Pro Ser Lys Phe Ser Gly Ser Gly Ser Gly
                 85                  90                  95

Thr Asp Tyr Ser Leu Thr Ile Ser Asn Leu Glu Gln Glu Asp Ile Ala
                100                 105                 110

Thr Tyr Phe Cys Gln Gln Gly Asn Thr Leu Pro Trp Thr Phe Ala Gly
                115                 120                 125

Gly Thr Lys Leu Glu Ile Lys Gly Gly Gly Ser Gly Gly Gly
        130                 135                 140

Ser Gly Gly Gly Ser Gly Gly Gly Ser Glu Val Gln Leu Gln
145                 150                 155                 160

Gln Ser Gly Pro Glu Leu Val Lys Pro Gly Ala Ser Met Lys Ile Ser
                165                 170                 175

Cys Lys Ala Ser Gly Tyr Ser Phe Thr Gly Tyr Thr Met Asn Trp Val
                180                 185                 190

Lys Gln Ser His Gly Lys Asn Leu Glu Trp Met Gly Leu Ile Asn Pro
                195                 200                 205

Tyr Lys Gly Val Ser Thr Tyr Asn Gln Lys Phe Lys Asp Lys Ala Thr
        210                 215                 220

Leu Thr Val Asp Lys Ser Ser Thr Ala Tyr Met Glu Leu Leu Ser
225                 230                 235                 240

Leu Thr Ser Glu Asp Ser Ala Val Tyr Tyr Cys Ala Arg Ser Gly Tyr
                245                 250                 255

Tyr Gly Asp Ser Asp Trp Tyr Phe Asp Val Trp Gly Gln Gly Thr Thr
                260                 265                 270

Leu Thr Val Phe Ser Thr Ser Gly Gly Gly Ser Gly Gly Gly
        275                 280                 285

Ser Gly Gly Gly Ser Gly Gly Gly Ser Asp Ile Met Ser Arg
290                 295                 300

Gly Ser Asp Leu Gly Lys Lys Leu Leu Glu Ala Ala Arg Ala Gly Gln
305                 310                 315                 320

Asp Asp Glu Val Arg Ile Leu Met Ala Asn Gly Ala Asp Val Asn Ala
                325                 330                 335

Lys Asp Glu Tyr Gly Leu Thr Pro Leu Tyr Leu Ala Thr Ala His Gly
                340                 345                 350

His Leu Glu Ile Val Glu Val Leu Leu Lys Asn Gly Ala Asp Val Asn
                355                 360                 365

Ala Val Asp Ala Ile Gly Phe Thr Pro Leu His Leu Ala Ala Phe Ile
        370                 375                 380

Gly His Leu Glu Ile Ala Glu Val Leu Leu Lys His Gly Ala Asp Val
385                 390                 395                 400

Asn Ala Gln Asp Lys Phe Gly Lys Thr Ala Phe Asp Ile Ser Ile Gly
                405                 410                 415

Asn Gly Asn Glu Asp Leu Ala Glu Ile Leu Gln Lys Leu Asn Glu Gln
                420                 425                 430

Lys Leu Ile Ser Glu Glu Asp Leu Asn Val Asp Gly Gly Gly Ser
        435                 440                 445

Gly Gly Gly Gly Ser Gly Gly Gly Ser Gly Gly Gly Ser Leu
450                 455                 460
```

Glu Ser Gly Gln Val Leu Leu Glu Ser Asn Ile Lys Val Leu Pro Thr
465                 470                 475                 480

Trp Ser Thr Pro Val Gln Pro Met Ala Leu Ile Val Leu Gly Gly Val
                485                 490                 495

Ala Gly Leu Leu Leu Phe Ile Gly Leu Gly Ile Phe Phe Cys Val Arg
            500                 505                 510

Cys Arg His Arg Arg Arg Gln Ala Glu Arg Met Ser Gln Ile Lys Arg
        515                 520                 525

Leu Leu Ser Glu Lys Lys Thr Cys Gln Cys Pro His Arg Phe Gln Lys
    530                 535                 540

Thr Cys Ser Pro Ile
545

<210> SEQ ID NO 5
<211> LENGTH: 54
<212> TYPE: DNA
<213> ORGANISM: Artificial Sequence
<220> FEATURE:
<223> OTHER INFORMATION: Synthetic

<400> SEQUENCE: 5
atggatttcc aggtccagat tttctccttc ctgctgattt ccgcaagcgt catt          54

<210> SEQ ID NO 6
<211> LENGTH: 18
<212> TYPE: PRT
<213> ORGANISM: Artificial Sequence
<220> FEATURE:
<223> OTHER INFORMATION: Synthetic

<400> SEQUENCE: 6

Met Asp Phe Gln Val Gln Ile Phe Ser Phe Leu Leu Ile Ser Ala Ser
1               5                   10                  15

Val Ile

<210> SEQ ID NO 7
<211> LENGTH: 387
<212> TYPE: DNA
<213> ORGANISM: Artificial Sequence
<220> FEATURE:
<223> OTHER INFORMATION: Synthetic

<400> SEQUENCE: 7
atgtcacggg gctccgacct gggcaaaaag ctgctggagg ccgctagggc cgggcaggac    60
gatgaagtga gaatcctgat ggccaacggg gctgacgtga atgctaagga tgagtacggc   120
ctgacccccc tgtatctggc tacagcacac ggccatctgg agatcgtgga agtcctgctg   180
aaaaacggag ccgacgtgaa tgcagtcgat gccattgggt tcactcctct gcacctggca   240
gcctttatcg acatctgga gattgcagaa gtgctgctga gcacggcgc tgacgtgaac    300 gcacaggata gttcggaaaa aaccgctttt gacatcagca ttggcaacgg aaatgaagac   360
ctggctgaaa tcctgcagaa actgaat                                        387

<210> SEQ ID NO 8
<211> LENGTH: 129
<212> TYPE: PRT
<213> ORGANISM: Artificial Sequence
<220> FEATURE:
<223> OTHER INFORMATION: Synthetic

<400> SEQUENCE: 8

```
Met Ser Arg Gly Ser Asp Leu Gly Lys Lys Leu Leu Glu Ala Ala Arg
1               5                   10                  15

Ala Gly Gln Asp Asp Glu Val Arg Ile Leu Met Ala Asn Gly Ala Asp
            20                  25                  30

Val Asn Ala Lys Asp Glu Tyr Gly Leu Thr Pro Leu Tyr Leu Ala Thr
        35                  40                  45

Ala His Gly His Leu Glu Ile Val Glu Val Leu Leu Lys Asn Gly Ala
    50                  55                  60

Asp Val Asn Ala Val Asp Ala Ile Gly Phe Thr Pro Leu His Leu Ala
65                  70                  75                  80

Ala Phe Ile Gly His Leu Glu Ile Ala Glu Val Leu Leu Lys His Gly
                85                  90                  95

Ala Asp Val Asn Ala Gln Asp Lys Phe Gly Lys Thr Ala Phe Asp Ile
            100                 105                 110

Ser Ile Gly Asn Gly Asn Glu Asp Leu Ala Glu Ile Leu Gln Lys Leu
        115                 120                 125

Asn
```

<210> SEQ ID NO 9
<211> LENGTH: 30
<212> TYPE: DNA
<213> ORGANISM: Artificial Sequence
<220> FEATURE:
<223> OTHER INFORMATION: Synthetic

<400> SEQUENCE: 9
gaacagaaac tgattagcga agaagacctg         30

<210> SEQ ID NO 10
<211> LENGTH: 10
<212> TYPE: PRT
<213> ORGANISM: Artificial Sequence
<220> FEATURE:
<223> OTHER INFORMATION: Synthetic

<400> SEQUENCE: 10

```
Glu Gln Lys Leu Ile Ser Glu Glu Asp Leu
1               5                   10
```

<210> SEQ ID NO 11
<211> LENGTH: 75
<212> TYPE: DNA
<213> ORGANISM: Artificial Sequence
<220> FEATURE:
<223> OTHER INFORMATION: Synthetic

<400> SEQUENCE: 11
aaccccgggg gaggaggagg gagcggggga ggaggcagcg gcggggagg ctctggagga    60 ggagggagcg gatcc                                                   75

<210> SEQ ID NO 12
<211> LENGTH: 25
<212> TYPE: PRT
<213> ORGANISM: Artificial Sequence
<220> FEATURE:
<223> OTHER INFORMATION: Synthetic

<400> SEQUENCE: 12

```
Asn Pro Gly Gly Gly Gly Gly Ser Gly Gly Gly Gly Ser Gly Gly
1               5                   10                  15
```

Gly Ser Gly Gly Gly Gly Ser Gly Ser
            20                  25

<210> SEQ ID NO 13
<211> LENGTH: 750
<212> TYPE: DNA
<213> ORGANISM: Artificial Sequence
<220> FEATURE:
<223> OTHER INFORMATION: Synthetic

<400> SEQUENCE: 13

```
atggacatcc agatgactca gaccacaagc tccctgtctg caagtctggg cgaccgggtg      60
acaatctcct gcagagcctc tcaggatatt aggaactacc tgaattggta tcagcagaaa     120
cctgatggca cagtcaagct gctgatctac ataccagcc ggctgcactc aggcgtgcca     180
agcaaattct caggaagcgg ctccgggact gactactccc tgaccatctc taacctggag     240
caggaagata ttgctaccta tttctgccag cagggcaata cactgccctg gactttttgcc    300
ggaggcacca aactggagat caaggggggga ggcggagtg gaggcggggg atcaggagga    360
ggaggcagcg gaggaggagg gtccgaggtc cagctgcagc agagcggacc agaactggtg    420
aagcccggag caagtatgaa aatctcctgt aaggcctcag gatacagctt caccggctat    480
acaatgaact gggtgaaaca gtcccatggc aagaacctgg aatggatggg gctgattaat    540
ccttacaaag cgtcagcac ctataatcag aagtttaaag acaaggccac actgactgtg    600
gataagtcta gttcaaccgc ttacatggag ctgctgtccc tgacatctga agacagtgcc    660
gtgtactatt gtgctcggtc tggctactat ggggacagtg attggtactt cgatgtctgg    720
ggacagggca ctaccctgac cgtgttttct                                       750
```

<210> SEQ ID NO 14
<211> LENGTH: 250
<212> TYPE: PRT
<213> ORGANISM: Artificial Sequence
<220> FEATURE:
<223> OTHER INFORMATION: Synthetic

<400> SEQUENCE: 14

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Ala Thr Tyr Phe Cys Gln Gln Gly Asn Thr Leu Pro
                85                  90                  95

Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
    130                 135                 140

Ser Met Lys Ile Ser Cys Lys Ala Ser Gly Tyr Ser Phe Thr Gly Tyr
145                 150                 155                 160

```
Thr Met Asn Trp Val Lys Gln Ser His Gly Lys Asn Leu Glu Trp Met
            165                 170                 175
Gly Leu Ile Asn Pro Tyr Lys Gly Val Ser Thr Tyr Asn Gln Lys Phe
            180                 185                 190
Lys Asp Lys Ala Thr Leu Thr Val Asp Lys Ser Ser Thr Ala Tyr
        195                 200                 205
Met Glu Leu Leu Ser Leu Thr Ser Glu Asp Ser Ala Val Tyr Tyr Cys
    210                 215                 220
Ala Arg Ser Gly Tyr Tyr Gly Asp Ser Asp Trp Tyr Phe Asp Val Trp
225                 230                 235                 240
Gly Gln Gly Thr Thr Leu Thr Val Phe Ser
            245                 250

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
actagtggcg gaggaggatc actcgag                                         27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

Thr Ser Gly Gly Gly Gly Ser Leu Glu
1               5

<210> SEQ ID NO 17
<211> LENGTH: 252
<212> TYPE: DNA
<213> ORGANISM: Artificial Sequence
<220> FEATURE:
<223> OTHER INFORMATION: Synthetic

<400> SEQUENCE: 17
agcggacagg tgctgctgga atccaatatc aaagtcctgc ccacttggtc taccccgtg      60 cagcctatgg ctctgattgt gctgggagga gtcgcaggac tgctgctgtt tatcgggctg   120
ggaattttct tttgcgtgcg ctgccggcac cggagaaggc aggccgagcg catgagccag   180
atcaagcgac tgctgagcga agagaaaacc tgtcagtgtc cccatagatt ccagaagacc   240
tgttcaccca tt                                                        252

<210> SEQ ID NO 18
<211> LENGTH: 84
<212> TYPE: PRT
<213> ORGANISM: Artificial Sequence
<220> FEATURE:
<223> OTHER INFORMATION: Synthetic

<400> SEQUENCE: 18

Ser Gly Gln Val Leu Leu Glu Ser Asn Ile Lys Val Leu Pro Thr Trp
1               5                   10                  15
Ser Thr Pro Val Gln Pro Met Ala Leu Ile Val Leu Gly Gly Val Ala
            20                  25                  30
```

```
Gly Leu Leu Leu Phe Ile Gly Leu Gly Ile Phe Phe Cys Val Arg Cys
         35                  40                  45

Arg His Arg Arg Arg Gln Ala Glu Arg Met Ser Gln Ile Lys Arg Leu
 50                  55                  60

Leu Ser Glu Lys Lys Thr Cys Gln Cys Pro His Arg Phe Gln Lys Thr
 65                  70                  75                  80

Cys Ser Pro Ile

<210> SEQ ID NO 19
<211> LENGTH: 56
<212> TYPE: PRT
<213> ORGANISM: Artificial Sequence
<220> FEATURE:
<223> OTHER INFORMATION: Synthetic

<400> SEQUENCE: 19

Gly Gly Gly Gly Ser Ala Glu Ala Ala Lys Glu Ala Ala Ala Lys
 1               5                  10                  15

Glu Ala Ala Ala Lys Glu Ala Ala Ala Lys Ala Leu Glu Ala Glu Ala
             20                  25                  30

Ala Ala Lys Glu Ala Ala Ala Lys Glu Ala Ala Lys Glu Ala Ala
         35                  40                  45

Ala Lys Ala Gly Gly Gly Gly Ser
 50                  55

<210> SEQ ID NO 20
<211> LENGTH: 55
<212> TYPE: PRT
<213> ORGANISM: Artificial Sequence
<220> FEATURE:
<223> OTHER INFORMATION: Synthetic

<400> SEQUENCE: 20

Gly Gly Gly Gly Ser Ala Ala Leu Ser Pro Ser Pro Leu Ala Pro Gly
 1               5                  10                  15

Pro Ala Ala Pro Ala Ala Leu Ala Pro Ala Pro Leu Ala Pro Gly Pro
             20                  25                  30

Ser Ala Pro Ala Ala Ala Ser Pro Ser Pro Leu Ala Pro Gly Pro Ser
         35                  40                  45

Ala Pro Gly Gly Gly Gly Ser
 50                  55

<210> SEQ ID NO 21
<211> LENGTH: 66
<212> TYPE: PRT
<213> ORGANISM: Artificial Sequence
<220> FEATURE:
<223> OTHER INFORMATION: Synthetic

<400> SEQUENCE: 21

Ser Gly Ala Val Leu Leu Ala Ser Ala Val Ala Val Leu Pro Ser Ala
 1               5                  10                  15

Ser Ser Pro Val Ala Pro Ser Gly Ala Val Leu Leu Ala Ser Ala Val
             20                  25                  30

Ala Val Leu Pro Ser Ala Ser Ser Pro Val Ala Pro Ser Gly Ala Val
         35                  40                  45

Leu Leu Ala Ser Ala Val Ala Val Leu Pro Ser Ala Ser Ser Pro Val
     50                  55                  60

Ala Pro
 65
```

<210> SEQ ID NO 22
<211> LENGTH: 729
<212> TYPE: DNA
<213> ORGANISM: Artificial Sequence
<220> FEATURE:
<223> OTHER INFORMATION: Synthetic

<400> SEQUENCE: 22

```
atgtctagac aggtacaact gcagcagtca ggacctgaac tgaagaagcc tggagagaca      60
gtcaagatct cctgcaaggc ctctgggtat cctttcacaa actatggaat gaactgggtg     120
aagcaggctc caggacaggg tttaaagtgg atgggctgga ttaacacctc cactggagag     180
tcaacatttg ctgatgactt caagggacgg tttgacttct ctttggaaac tctgccaac     240
actgcctatt tgcagatcaa caacctcaaa agtgaagaca tggctacata tttctgtgca     300
agatgggagg tttaccacgg ctacgttcct tactggggcc aagggaccac ggtcaccgtt     360
tcctctggcg gtggcggttc tggtggcggt ggctccggcg gtggcggttc tgacatccag     420
ctgacccagt ctcacaaatt cctgtccact tcagtaggag acagggtcag catcacctgc     480
aaggccagtc aggatgtgta atgctgtt gcctggtatc aacagaaacc aggacaatct     540
cctaaacttc tgatttactc ggcatcctcc cggtacactg gagtcccttc tcgcttcact     600
ggcagtggct ctgggccgga tttcactttc accatcagca gtgtgcaggc tgaagacctg     660
gcagtttatt tctgtcagca acattttcgt actccattca cgttcggctc ggggacaaaa     720
ttggagatc                                                             729
```

<210> SEQ ID NO 23
<211> LENGTH: 243
<212> TYPE: PRT
<213> ORGANISM: Artificial Sequence
<220> FEATURE:
<223> OTHER INFORMATION: Synthetic

<400> SEQUENCE: 23

```
Met Ser Arg Gln Val Gln Leu Gln Gln Ser Gly Pro Glu Leu Lys Lys
1               5                   10                  15

Pro Gly Glu Thr Val Lys Ile Ser Cys Lys Ala Ser Gly Tyr Pro Phe
            20                  25                  30

Thr Asn Tyr Gly Met Asn Trp Val Lys Gln Ala Pro Gly Gln Gly Leu
        35                  40                  45

Lys Trp Met Gly Trp Ile Asn Thr Ser Thr Gly Glu Ser Thr Phe Ala
    50                  55                  60

Asp Asp Phe Lys Gly Arg Phe Asp Phe Ser Leu Glu Thr Ser Ala Asn
65                  70                  75                  80

Thr Ala Tyr Leu Gln Ile Asn Asn Leu Lys Ser Glu Asp Met Ala Thr
                85                  90                  95

Tyr Phe Cys Ala Arg Trp Glu Val Tyr His Gly Tyr Val Pro Tyr Trp
            100                 105                 110

Gly Gln Gly Thr Thr Val Thr Val Ser Ser Gly Gly Gly Gly Ser Gly
        115                 120                 125

Gly Gly Gly Ser Gly Gly Gly Gly Ser Asp Ile Gln Leu Thr Gln Ser
    130                 135                 140

His Lys Phe Leu Ser Thr Ser Val Gly Asp Arg Val Ser Ile Thr Cys
145                 150                 155                 160

Lys Ala Ser Gln Asp Val Tyr Asn Ala Val Ala Trp Tyr Gln Gln Lys
                165                 170                 175
```

Pro Gly Gln Ser Pro Lys Leu Leu Ile Tyr Ser Ala Ser Ser Arg Tyr
            180                 185                 190

Thr Gly Val Pro Ser Arg Phe Thr Gly Ser Gly Ser Gly Pro Asp Phe
            195                 200                 205

Thr Phe Thr Ile Ser Ser Val Gln Ala Glu Asp Leu Ala Val Tyr Phe
            210                 215                 220

Cys Gln Gln His Phe Arg Thr Pro Phe Thr Phe Gly Ser Gly Thr Lys
225                 230                 235                 240

Leu Glu Ile

<210> SEQ ID NO 24
<211> LENGTH: 750
<212> TYPE: DNA
<213> ORGANISM: Artificial Sequence
<220> FEATURE:
<223> OTHER INFORMATION: Synthetic

<400> SEQUENCE: 24
atggacatcc agatgactca gaccacaagc tccctgtctg caagtctggg cgaccgggtg      60
acaatctcct gcagagcctc tcaggatatt aggaactacc tgaattggta tcagcagaaa     120
cctgatggca cagtcaagct gctgatctac tataccagcc ggctgcactc aggcgtgcca     180
agcaaattct caggaagcgg ctccgggact gactactccc tgaccatctc taacctggag     240
caggaagata ttgttaccta tttctgccag cagggcaata cactgccctg gacttttgcc     300
ggaggcacca aactggagat caaggggggga ggcggggagtg gaggcggggg atcaggagga     360
ggaggcagcg gaggaggagg gtccgaggtc cagctgcagc agagcggacc agaactggtg     420
aagcccggag caagtatgaa aatctcctgt aaggcctcag gatacagctt caccggctat     480
ccgatgaact gggtgaaaca gtcccatggc aagaacctgg aatggatggg gctgattaat     540
ccttacaaag cgtcagcac ctataatcag aagtttaaag acaaggccac actgactgtg     600
gataagtcta gttcaaccgc ttacatggag ctgctgtccc tgacatctga agacagtgcc     660
gtgtactatt gtgctcggtc tggctactat ggggacagtg attggtactt cgatgtctgg     720
ggacagggca ctaccctgac cgtgttttct                                      750

<210> SEQ ID NO 25
<211> LENGTH: 250
<212> TYPE: PRT
<213> ORGANISM: Artificial Sequence
<220> FEATURE:
<223> OTHER INFORMATION: Synthetic

<400> SEQUENCE: 25

Met Asp Ile Gln Met Thr Gln Thr Thr Ser Ser Leu Ser Ala Ser Leu
1               5                   10                  15

Gly Asp Arg Val Thr Ile Ser Cys Arg Ala Ser Gln Asp Ile Arg Asn
            20                  25                  30

Tyr Leu Asn Trp Tyr Gln Gln Lys Pro Asp Gly Thr Val Lys Leu Leu
        35                  40                  45

Ile Tyr Tyr Thr Ser Arg Leu His Ser Gly Val Pro Ser Lys Phe Ser
    50                  55                  60

Gly Ser Gly Ser Gly Thr Asp Tyr Ser Leu Thr Ile Ser Asn Leu Glu
65                  70                  75                  80

Gln Glu Asp Ile Val Thr Tyr Phe Cys Gln Gln Gly Asn Thr Leu Pro
                85                  90                  95

```
Trp Thr Phe Ala Gly Gly Thr Lys Leu Glu Ile Lys Gly Gly Gly Gly
            100                 105                 110

Ser Gly Gly Gly Gly Ser Gly Gly Gly Ser Gly Gly Gly Gly Ser
        115                 120                 125

Glu Val Gln Leu Gln Gln Ser Gly Pro Glu Leu Val Lys Pro Gly Ala
        130                 135                 140

Ser Met Lys Ile Ser Cys Lys Ala Ser Gly Tyr Ser Phe Thr Gly Tyr
145                 150                 155                 160

Pro Met Asn Trp Val Lys Gln Ser His Gly Lys Asn Leu Glu Trp Met
                165                 170                 175

Gly Leu Ile Asn Pro Tyr Lys Gly Val Ser Thr Tyr Asn Gln Lys Phe
            180                 185                 190

Lys Asp Lys Ala Thr Leu Thr Val Asp Lys Ser Ser Ser Thr Ala Tyr
        195                 200                 205

Met Glu Leu Leu Ser Leu Thr Ser Glu Asp Ser Ala Val Tyr Tyr Cys
        210                 215                 220

Ala Arg Ser Gly Tyr Tyr Gly Asp Ser Asp Trp Tyr Phe Asp Val Trp
225                 230                 235                 240

Gly Gln Gly Thr Thr Leu Thr Val Phe Ser
                245                 250
```

TRIFUNCTIONAL T CELL-ANTIGEN COUPLER AND METHODS AND USES THEREOF

RELATED APPLICATIONS

This application is a continuation of U.S. application Ser. No. 15/117,173 filed on Aug. 5, 2016, now issued as of U.S. Pat. No. 10,435,453 on Oct. 8, 2019, which is a national stage entry of International Application No. PCT/CA2015/000068 filed on Feb. 6, 2015, which claims priority to U.S. Provisional Patent Application No. 61/936,906 filed on Feb. 7, 2014, the contents of which are hereby incorporated by reference in their entirety.

FIELD

The present disclosure relates to a method of treating cancer by engineering T-cells with high cytotoxicity against specific target cells and reduced off-target toxicity. In particular, the disclosure relates to engineering T-cells to express novel biological agents which mimic the natural T-cell activation process.

BACKGROUND

Cancer is a major health challenge, with over 150,000 cases of cancer expected to be diagnosed in Canada in 2013 alone. While patients with early stage disease can be treated effectively by conventional therapies (surgery, radiation, chemotherapy), few options are available to patients with advanced disease and those options are typically palliative in nature. Active immunotherapy seeks to employ the patient's immune system to clear tumor deposits and offers an exciting option to patients who have failed conventional therapies (Humphries, 2013). Indeed, several clinical studies have demonstrated that immunotherapy with T cells can be curative in patients with advanced melanoma, confirming the utility of this approach (Humphries, 2013). Additionally, patients suffering from chronic lymphocytic leukemia (CLL) and acute lymphoblastic leukemia (ALL) have also been effectively treated and cured with T cell immunotherapy (Fry and Mackall, 2013)(Kochenderfer and Rosenberg, 2013). While there are several immunotherapy approaches, the engineering of T cells with chimeric receptors allows any patient's immune cells to be targeted against any desirable target in a major histocompatibility complex (MHC) independent manner. To date, the chimeric receptors used for engineering T cells consist of a targeting domain, usually a single-chain fragment variable (scFv); a transmembrane domain; and a cytosolic domain that contains signaling elements from the T cell receptor and associated proteins (Dotti et al., 2009). Such chimeric receptors have been referred to as "T-body", "Chimeric Antigen Receptor" (CAR) or "Chimeric Immune Receptor" (CIR)—currently, most researchers use the term "CAR" (Dotti et al., 2009). These CARs are considered in modular terms and scientists have spent considerable time investigating the influence of different cytoplasmic signaling domains on CAR function. The first-generation CARs employed a single signaling domain from either CD3ζ or FcεRIγ. Second-generations CARs combined the signaling domain of CD3ζ with the cytoplasmic domain of costimulatory receptors from either the CD28 or TNFR family of receptors (Dotti et al., 2009). Third-generation CARs combined multiple costimulatory domains, but there is concern that third-generation CARs may lose antigen-specificity (Han et al., 2013). Most CAR-engineered T cells that are being tested in the clinic employ second-generation CARs where CD3ζ is coupled to the cytoplasmic domain of either CD28 or CD137 (Han et al., 2013)(Finney et al., 2004)(Milone et al., 2009).

While CAR-engineered T cells have shown considerable promise in clinical application, they rely on a synthetic method for replacing the activation signal that is provided by the T cell receptor (TCR). Since this synthetic receptor does not deliver all of the signaling components associated with the TCR (ex. CD3 epsilon, Lck), it remains unclear whether the T cells are optimally activated by the CAR or how the CAR activation affects T cell differentiation (ex. progression to memory). Furthermore, since the CAR signaling domains are disconnected from their natural regulatory partners by the very nature of the CAR structure, there is also an inherent risk that CARs may lead to a low-level of constitutive activation which could result in off-target toxicities.

Given these limitations, it is preferable to re-direct T cells to attack tumors via their natural TCR. To this end, a class of recombinant proteins termed "Bispecific T-cell Engagers" (BiTEs) has been created (Chames and Baty, 2009)(Portell et al., 2013). These proteins employ bispecific antibody fragments to crosslink T-cell TCR receptors with target antigens. This leads to efficient T-cell activation, triggering cytotoxicity. Similarly, bi-specific antibodies have been generated that accomplish this goal and some scientists have simply linked anti-CD3 antibodies to tumor-specific antibodies employing chemical linkage (Chames and Baty, 2009). While these bi-specific proteins have demonstrated some activity in vitro, GMP production, short biological half-lives and bioavailability represent significant challenges to the successful use of these molecules in cancer treatment. Additionally, these molecules also fail to properly recapitulate natural TCR signaling because they do not engage the TCR co-receptors (CD8 and CD4).

Accordingly, a need remains for T cell-antigen couplers with enhanced activity and safety compared to traditional CARs.

SUMMARY

The present inventors have demonstrated that a trifunctional T cell-antigen coupler that better mimics the natural signaling through the T cell receptor (TCR), while retaining major histocompatibility complex unrestricted targeting, has enhanced activity and safety compared to traditional chimeric antigen receptors.

Accordingly, one aspect of the disclosure provides a nucleic acid comprising:
  a. a first polynucleotide encoding a target-specific ligand;
  b. a second polynucleotide encoding a ligand that binds a protein associated with the TCR complex; and
  c. a third polynucleotide encoding a T cell receptor signaling domain polypeptide.

Another aspect of the disclosure provides a polypeptide encoded by the nucleic acid described above.

Another aspect of the disclosure provides an expression vector comprising the nucleic acid described above.

Yet another aspect of the disclosure provides a T-cell expressing the nucleic acid described above. Another aspect of the disclosure provides a pharmaceutical composition comprising the T cell and a carrier.

The disclosure also provides a use of a T cell for treating cancer in a subject in need thereof, wherein the T cell expresses a nucleic acid comprising:
   a. a first polynucleotide encoding a target-specific ligand;
   b. a second polynucleotide encoding a ligand that binds a protein associated with the TCR complex; and
   c. a third polynucleotide encoding a T cell receptor signaling domain polypeptide.

In one embodiment, the target-specific ligand binds an antigen on a cancerous cell.

In another embodiment, the target-specific ligand is a designed ankyrin repeat (DARPin) polypeptide or scFv.

In another embodiment, the protein associated with the TCR complex is CD3.

In another embodiment, the ligand that binds a protein associated with the TCR complex is a single chain antibody.

In another embodiment, the ligand that binds a protein associated with the TCR complex is UCHT1, or a variant thereof.

In another embodiment, the T cell receptor signaling domain polypeptide comprises a cytosolic domain and a transmembrane domain.

In another embodiment, the cytosolic domain is a CD4 cytosolic domain and the transmembrane domain is a CD4 transmembrane domain.

In another embodiment the first polynucleotide and third polynucleotide are fused to the second polynucleotide.

In another embodiment, the second polynucleotide and third polynucleotide are fused to the first polynucleotide.

The disclosure also provides a vector construct comprising:
   a. a first polynucleotide encoding a target-specific ligand;
   b. a second polynucleotide encoding a ligand that binds a protein associated with the TCR complex; and
   c. a third polynucleotide encoding a T cell receptor signaling domain polypeptide, and
   d. a promoter functional in a mammalian cell.

In one embodiment, the first polynucleotide and third polynucleotide are fused to the second polynucleotide to provide a T cell antigen coupler fusion and the coding sequence of the T cell antigen coupler fusion is operably connected to the promoter.

In another embodiment, the second polynucleotide and third polynucleotide are fused to the first polynucleotide to provide a T cell antigen coupler fusion and the coding sequence of the T cell antigen coupler fusion is operably connected to the promoter.

The disclosure also provides an isolated T cell transfected with the vector construct.

Other features and advantages of the present disclosure will become apparent from the following detailed description. It should be understood, however, that the detailed description and the specific examples while indicating preferred embodiments of the disclosure are given by way of illustration only, since various changes and modifications within the spirit and scope of the disclosure will become apparent to those skilled in the art from this detailed description.

BRIEF DESCRIPTION OF THE DRAWINGS

FIGS. 1A-D is a graphic summary of the trifunctional T cell-antigen coupler (Tri-TAC) in comparison with a conventional second-generation CAR. A schema of the constructs used in this work is included.

FIGS. 3A-B show an analysis of cell activation looking at the different markers IFN-γ, TNF-α and CD107a.

FIGS. 7A-C show the functionality of scFv CD4 TAC. (7A) is a histogram showing surface expression of the scFv CD4 TAC receptor relative to empty vector, (7B) shows antigen specific activation of T-cells expressing either the scFv CD4 TAC (top) or scFV CAR (bottom) and (7C) shows comparable killing of MCF-7 human tumour cell line (Her2 positive) by both scFv CD4 TAC and scFv CAR.

FIG. 13 shows Lck interaction with TAC variants. The top panel shows the ability of full length TAC and the cytosolic deletion to pull down Lck and the bottom panel is a densitometry analysis of Lck detected in the pellets of.

FIGS. 16A-C shows enhanced surface expression of the A85V, T161P mutant. (16A) compares final CD/CD8 populations between CD4 TAC and A85V, T161P mutant, (16B) shows enhanced surface expression of the A85V, T161P mutant and (16C) shows that cytokine production is diminished in the A85V, T161 mutant.

DETAILED DESCRIPTION (i) Definitions

Figure 2:
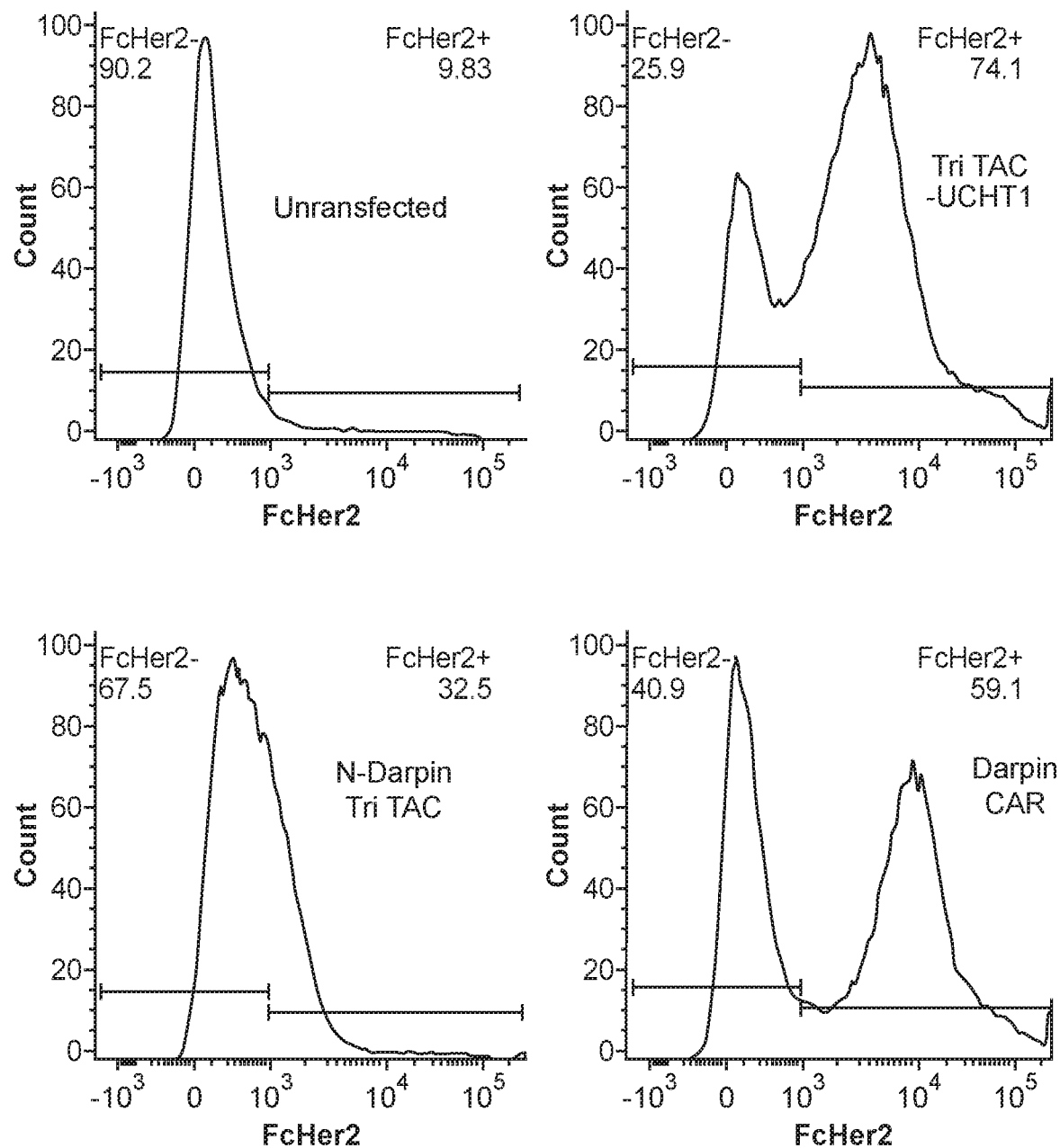
FIG. 2 shows a surface expression analysis of the Tri-TAC variants and the classical CAR.

The term "a cell" as used herein includes a single cell as well as a plurality of cells.

The term "T cell" as used herein refers to a type of lymphocyte that plays a central role in cell-mediated immunity. T cells, also referred to as T lymphocytes, can be distinguished from other lymphocytes, such as B cells and natural killer cells, by the presence of a T-cell receptor (TCR) on the cell surface. There are several subsets of T cells with distinct functions, including but not limited to, T helper cells, cytotoxic T cells, memory T cells, regulatory T cells and natural killer T cells.

The term "T cell antigen coupler" as used herein refers to an engineered nucleic acid construct or polypeptide, that when expressed on a T cell, targets the T cell to a particular antigen.

The term "polynucleotide" and/or "nucleic acid sequence" and/or "nucleic acid" as used herein refers to a sequence of nucleoside or nucleotide monomers consisting of bases, sugars and intersugar (backbone) linkages. The term also includes modified or substituted sequences comprising non-naturally occurring monomers or portions thereof. The nucleic acid sequences of the present application may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acids of the present disclosure may be isolated from biological organisms, formed by laboratory methods of genetic recombination or obtained by chemical synthesis or other known protocols for creating nucleic acids.

The term "isolated polynucleotide" or "isolated nucleic acid sequence" as used herein refers to a nucleic acid substantially free of cellular material or culture medium when produced by recombinant DNA techniques, or chemical precursors, or other chemicals when chemically synthesized. An isolated nucleic acid is also substantially free of sequences which naturally flank the nucleic acid (i.e. sequences located at the 5' and 3' ends of the nucleic acid) from which the nucleic acid is derived. The term "nucleic acid" is intended to include DNA and RNA and can be either double stranded or single stranded, and represents the sense or antisense strand. Further, the term "nucleic acid" includes the complementary nucleic acid sequences.

The term "recombinant nucleic acid" or "engineered nucleic acid" as used herein refers to a nucleic acid or polynucleotide that is not found in a biological organism. For example, recombinant nucleic acids may be formed by laboratory methods of genetic recombination (such as molecular cloning) to create sequences that would not otherwise be found in nature. Recombinant nucleic acids may also be created by chemical synthesis or other known protocols for creating nucleic acids.

The term "polypeptide" or "protein" as used herein describes a chain of amino acids that correspond to those encoded by a nucleic acid. A polypeptide or protein of this disclosure can be a peptide, which usually describes a chain of amino acids of from two to about 30 amino acids. The term protein as used herein also describes a chain of amino acids having more than 30 amino acids and can be a fragment or domain of a protein or a full length protein. Furthermore, as used herein, the term protein can refer to a linear chain of amino acids or it can refer to a chain of amino acids that has been processed and folded into a functional protein. It is understood, however, that 30 is an arbitrary number with regard to distinguishing peptides and proteins and the terms can be used interchangeably for a chain of amino acids. The proteins of the present disclosure can be obtained by isolation and purification of the proteins from cells where they are produced naturally, by enzymatic (e.g., proteolytic) cleavage, and/or recombinantly by expression of nucleic acid encoding the proteins or fragments of this disclosure. The proteins and/or fragments of this disclosure can also be obtained by chemical synthesis or other known protocols for producing proteins and fragments.

The term "isolated polypeptide" refers to a polypeptide substantially free of cellular material or culture medium when produced by recombinant DNA techniques, or chemical precursors or other chemicals when chemically synthesized.

The term "antibody" as used herein is intended to include monoclonal antibodies, polyclonal antibodies, single chain antibodies, chimeric antibodies and antibody fusions. The antibody may be from recombinant sources and/or produced in transgenic animals. The term "antibody fragment" as used herein is intended to include without limitations Fab, Fab', $F(ab)_2$, scFv, dsFv, ds-scFv, dimers, minibodies, diabodies, and multimers thereof, multispecific antibody fragments and Domain Antibodies.

The term "vector" as used herein refers to a polynucleotide that can be used to deliver a nucleic acid to the inside of a cell. In one embodiment, a vector is an expression vector comprising expression control sequences (for example, a promoter) operatively linked to a nucleic acid to be expressed in a cell. Vectors known in the art include, but are not limited to, plasmids, phages, cosmids and viruses.

(ii) Compositions

The present inventors have developed a Trifunctional T cell-antigen coupler (Tri-TAC) to better mimic the natural signaling through the T-cell receptor (TCR), while retaining MHC unrestricted targeting. Specifically, the inventors created a molecule where the transmembrane and intracellular regions of the CD4 co-receptor, which localize to the lipid raft and bind Lck, respectively, were fused to single-chain antibody that binds CD3. The construct is designed to draw the CD3 molecule and the TCR into regions of lipid rafts and bring Lck into the proximity of the TCR, similar to natural MHC binding. To target the chimeric receptor, a designed ankyrin repeat (DARPin) was linked to the CD4-UCHT1 chimera to generate a tri-functional T cell-antigen coupler (Tri-TAC).

Experimentally, human T cells were engineered to express either the prototype Tri-TAC or a conventional CAR with the same DARPin. It was determined that in all aspects, T cells engineered with the Tri-TAC demonstrated functionality equivalent to a conventional CAR. With regard to two parameters (TNF-α production and CD107a mobilization), it was observed that the Tri-TAC was more active than a conventional CAR. Further, the data shows that on a per molecule basis the Tri-TAC shows a significantly enhanced activity. Additionally the Tri-TAC offers enhanced safety compared to traditional CARs as no activation domains are part of the protein.

Accordingly, the present disclosure relates to a nucleic acid comprising:

a first polynucleotide encoding a target-specific ligand;
a second polynucleotide encoding a ligand that binds the TCR complex; and
a third polynucleotide encoding a T cell receptor signaling domain polypeptide.

In one embodiment, the nucleic acid is a recombinant, or engineered, nucleic acid. In another embodiment, the first, second and/or third polynucleotides are recombinant, or engineered, polynucleotides.

The disclosure also relates to a polypeptide encoded by the nucleic acid and a composition comprising the nucleic acid.

A nucleic acid comprising each of the first, second and third polynucleotides, and the polypeptide encoded by the nucleic acid is also referred to herein as a Trifunctional T cell-antigen coupler or Tri-TAC.

Target-Specific Ligand

The target-specific ligand directs the T cell-antigen coupler to a target cell. Accordingly, a target-specific ligand refers to any substance that binds, directly or indirectly, to a target cell. A target cell may be any cell associated with a disease state, including, but not limited to cancer. In one embodiment, the target specific ligand binds to an antigen (protein produced by a cell that can elicit an immune response) on the target cell. The target-specific ligand can also be referred to as an antigen binding domain.

In one embodiment, a target cell is a tumor cell. Here, a target-specific ligand can bind to a tumor antigen or tumor associated antigen on a tumor cell. Tumor antigens are well known in the art. The term "tumor antigen" or "tumor associated antigen" as used herein means any antigenic substance produced in tumor cells that triggers an immune response in a host (e.g. which can be represented by MHC complexes). The tumor antigen when proteinaceous can for example be a sequence of 8 or more amino acids up to the full protein and any number of amino acids in between 8 and the full length protein which comprises at least one antigenic fragment of the full length protein that can be represented in a MHC complex. Examples of tumor antigens include, but are not limited to, HER2 (erbB-2), B-cell maturation antigen (BCMA), alphafetoprotein (AFP), carcinoembryonic antigen (CEA), CA-125, MUC-1, epithelial tumor antigen (ETA), tyrosinase, melanoma-associated antigen (MAGE), prostate-specific antigen (PSA), glioma-associated antigen, (β-human chorionic gonadotropin, thyroglobulin, RAGE-1, MN-CA IX, human telomerase reverse transcriptase, RU1, RU2 (AS), intestinal carboxyl esterase, mut hsp70-2, M-CSF, prostase, PAP, NY-ESO-1, LAGE-1a, p53, prostein, PSMA, survivin and telomerase, prostate-carcinoma tumor antigen-1 (PCTA-1), ELF2M, neutrophil elastase, CD22, insulin growth factor (IGF)-I, IGF-II, IGF-I receptor and mesothelin.

Examples of target-specific ligands include antibodies and fragments thereof, for example single chain antibodies such as scFVs, or small proteins that bind to the target cell and/or antigen.

One example of a target-specific ligand is a designed ankyrin [0063] repeat (DARPin) targeted to a specific cell and/or antigen. In one embodiment, the target-specific ligand is a DARPin targeted to HER2 (erbB-2). One example of a DARPin targeted to HER2 (erb-2) is provided herein as SEQ ID NO: 7 and 8.

Another example of a target-specific ligand is a scFV targeted to [0064] a specific cell and/or antigen. In one embodiment, the target-specific ligand is a scFv that binds HER2 (erb-2). One example of an scFv that binds HER2 (erb-2) is provided herein as SEQ ID NO: 22 and 23.

Ligand that Binds the TCR Complex

The T cell-antigen coupler is designed to recruit the T-Cell Receptor (TCR) in combination with co-receptor stimulation. Accordingly, the T cell antigen coupler includes a ligand that binds a protein associated with the T-cell receptor complex.

The TCR (T-Cell Receptor) is a complex of integral membrane proteins that participates in the activation of T cells in response to the binding of an antigen. The TCR is a disulfide-linked membrane-anchored heterodimer normally consisting of the highly variable alpha (α) and beta (β) chains expressed as part of a complex with the invariant CD3 (cluster of differentiation 3) chain molecules. T cells expressing this receptor are referred to as α:β (or αβ T cells, though a minority of T cells express an alternate receptor, formed by variable gamma (γ) and delta (δ) chains, referred as γδ T cells. CD3 is a protein complex composed of four distinct chains. In mammals, the complex contains a CD3γ chain, a CD3δ chain, and two CD3ε chains.

As used herein, the term "ligand that binds a protein associated with the T-cell receptor complex" includes any substance that binds, directly or indirectly, to a protein of the TCR. Proteins associated with the TCR include, but are not limited to the TCR alpha (α) chain, TCR beta (β) chain, TCR gamma (γ) chain, TCR delta (δ) chain, CD3γ chain, CD3δ chain and CD3ε chains. In one embodiment, a ligand that binds a protein associated with the T-cell receptor complex is an antibody to the TCR alpha (α) chain, TCR beta (β) chain, TCR gamma (γ) chain, TCR delta (δ) chain, CD3γ chain, CD3δ chain and/or CD3E chain.

In one embodiment, the ligand is an antibody or a fragment thereof that binds CD3. Examples of CD3 antibodies are known in the art (for muromonab, otelixizumab, teplizumab and visilizumab). In one embodiment, the antibody that binds CD3 is a single chain antibody, for example a singlechain variable fragment (scFv).

Another example of a CD3 antibody is UCHT1 which targets CD3ε. A sequence for UCHT1 is provided herein as SEQ ID NOs: 13 and 14.

T Cell Receptor Signaling Domain Polypeptide

The T cell antigen coupler includes a T cell receptor signaling domain polypeptide. As used herein, the term "T cell receptor signaling domain" refers to a polypeptide that (a) localizes to the lipid raft and/or (b) binds Lck. A T cell receptor signaling domain polypeptide can include one or more protein domains including, but not limited to, a cytoplasmic domain and/or a transmembrane domain. As used herein, "protein domain" refers to a conserved part of a given protein sequence structure that can function and exist independently of the rest of the protein chain. In one embodiment, the T cell receptor signaling domain polypeptide includes a cytoplasmic domain. In another embodiment, the T cell receptor signaling domain polypeptide includes a transmembrane domain. In a further embodiment, the T cell receptor signaling domain polypeptide includes both a cytoplasmic and a transmembrane domain.

T cell receptor signaling domain polypeptides include TCR co-receptors and co-stimulators and TCR co-receptor and co-stimulator protein domains.

A "TCR co-receptor" refers to a molecule that assists the T cell receptor (TCR) in communicating with an antigen-presenting cell. Examples of TCR co-receptors include, but are not limited to, CD4, CD8, CD28, CD45, CD4, CD5, CDS, CD9, CD16, CD22, CD33, CD37, CD64, CD80, CD86, CD134, CDt 37 and CD 154.

A "TCR co-stimulator" refers to a molecule that is required for the response of a T cell to an antigen. Examples of TCR co-stimulators include, but are not limited to, PD-1, ICOS, CD27, CD28, 4-1BB (CD 137), OX40, CD30, CD40, lymphocyte fiction-associated antigen 1 (LFA-1), CD2, CD7, LIGHT, NKG2C, B7-H3, and a ligand that specifically binds CD83.

In one embodiment, the T cell receptor signaling domain polypeptide includes both a cytoplasmic domain and a transmembrane domain of a TCR co-receptor or co-stimulator protein. The cytoplasmic domain and transmembrane domain may be from the same co-receptor or co-stimulator or from different co-receptors or co-stimulators. The cytoplasmic domain and transmembrane domains are optionally joined by a linker.

In one embodiment, the T cell receptor signaling domain polypeptide comprises the transmembrane and cytoplasmic domains of the CD4 co-receptor (see for example SEQ ID NO: 17 and 18).

In another embodiment, the T cell receptor signaling domain polypeptide comprises the transmembrane and cytoplasmic domains of the CD8a co-receptor.

In other embodiment, the cytoplasmic and/or transmembrane domain of the T cell receptor signaling domain polypeptide is synthetic. For example, the transmembrane domain is optionally a synthetic, highly hydrophobic membrane domain.

In another example, the transmembrane domain is a glycophorine transmembrane domain. In yet another example the T cell receptor signaling domain polypeptide includes a CD48 GPI signal sequence to attach the T-cell antigen coupler to the membrane using the GPI anchor.

In addition to the three components of the T cell antigen coupler described herein (target-specific ligand, ligand that binds the TCR complex and T cell receptor signaling domain polypeptide), it is contemplated that other polypeptides could also be included. For example, the T cell antigen coupler optionally includes additional polypeptides that directly or indirectly act to target or activate the T cell.

Linkers

The various components of the T cell antigen coupler can be fused directly to each other, or they may be joined by at least one linker, optionally a peptide linker. The peptide linker can be of any size provided it does not interfere with the function of the individual linked components. In one embodiment, the peptide linker is from about 1 to about 15 amino acids in length, more specifically from about 1 to about 10 amino acids, and most specifically from about 1 to about 6 amino acids.

Examples of linkers useful in the T cell antigen coupler include the G4S3 linker. Other examples of linkers are peptides corresponding to SEQ ID NOs: 11, 12, 15, 16, 19, 20 and 21 and variants and fragments thereof.

Configuration

The T cell-antigen coupler may be present in various configurations as will be readily appreciated by a person of skill in the art.

In one embodiment, the target specific ligand and the T cell receptor signaling domain polypeptide are both fused to the ligand that binds the TCR complex. For example, the N-DARPin TAG described here (also referred to as configuration 1; SEQ ID NO: 1 and 2) includes, in order:

i) N-Darpin Tri TAG leader sequence (secretion signal) (SEQ ID NO: 5 and 6)

ii) DARPin specific for Her2 antigen (SEQ ID NO: 7 and 8)

iii) Myc tag (SEQ ID NO: 9 and 10)

iv) Linker 1 (SEQ ID NO: 11 and 12)

v) UCHT1 (SEQ ID NO: 13 and 14)

vi) Linker 2 (SEQ ID NO: 15 and 16)

vii) CD4 (SEQ ID NO: 17 and 18)

In another embodiment, the DARPin is replaced with a scFV ScFv specific for a Her2 antigen (SEQ ID NO: 22 and 23).

In another embodiment, the ligand that binds the TCR complex and the T cell receptor signaling domain polypeptide are both fused to the target specific ligand (C-DARPin TAG as described here (also referred to as configuration 1; SEQ ID NO: 3 and 4)). Alternative configurations will be readily apparent to a person of skill in the art.

Vector Constructs

A variety of delivery vectors and expression vehicles can be employed to introduce nucleic acids described herein into a cell. Accordingly, the aforementioned polynucleotides are optionally comprised in a vector to provide a vector construct, also herein referred to as a vector.

Therefore, the present disclosure also relates to a vector comprising:

a. a first polynucleotide encoding a target-specific ligand;

b. a second polynucleotide encoding an antibody that binds CD3; and c. a third polynucleotide encoding a T cell receptor signaling domain polypeptide, and optionally a promoter functional in a mammalian cell.

Promoters, regions of DNA that initiate transcription of a particular nucleic acid sequence, are well known in the art. A "promoter functional in a mammalian cell" refers to a promoter that drives expression of the associated nucleic acid sequence in a mammalian cell. A promoter that drives expression of a nucleic acid sequence may be referred to as being "operably connected" to the nucleic acid sequence.

In one embodiment, the first polynucleotide and third polynucleotide are fused to the second polynucleotide to provide a T cell antigen coupler fusion and the coding sequence of the T cell antigen coupler fusion is operably connected to the promoter.

In another embodiment, the second polynucleotide and third polynucleotide are fused to the first polynucleotide to provide a T cell antigen coupler fusion and the coding sequence of the T cell antigen coupler fusion is operably connected to the promoter.

Optionally, the vector is designed for expression in mammalian cells such as T cells. In one embodiment, the vector is a viral vector, optionally a retroviral vector.

Vectors that are useful comprise vectors derived from lentiviruses, Murine Stem Cell Viruses (MSCV), pox viruses, oncoretroviruses, adenoviruses, and adeno-associated viruses. Other delivery vectors that are useful comprise vectors derived from herpes simplex viruses, transposons, vaccinia viruses, human papilloma virus, Simian immunodeficiency viruses, HTLV, human foamy virus and variants thereof. Further vectors that are useful comprise vectors derived from spumaviruses, mammalian type B retroviruses, mammalian type C retroviruses, avian type C retroviruses, mammalian type D retroviruses and HTLV/BLV type retroviruses. One example of a lentiviral vector useful in the disclosed compositions and methods is the pCCL vector.

Variations of Polynucleotides and Polypeptides

Many modifications may be made to the polynucleotide sequences including vector sequences and polypeptides sequences disclosed in this application and these will be apparent to one skilled in the art. Modifications include substitution, insertion or deletion of nucleotides or amino acids or altering the relative positions or order of nucleotides or amino acids.

In one embodiment, the polynucleotides described herein may be modified or mutated to optimize the function of the encoded polypeptide and/or the function, activity and/or expression of the T cell antigen coupler.

Figure 15A:
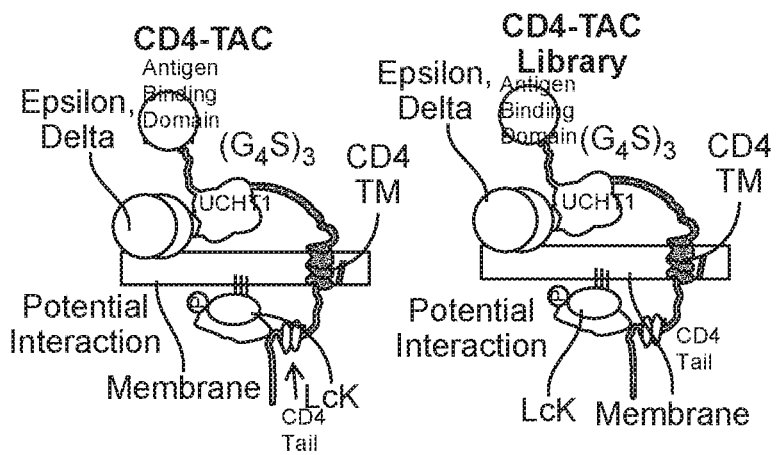
FIGS. 15A-C shows wild type CD4 TAC compared to a random mutagen library of UCHT1. (15A) shows the schematic representation of the mutant, (15B) is a histogram showing surface expression of the library and (15C) shows the ability of the library to activate T cells and produce cytokines.
Figure 15B:
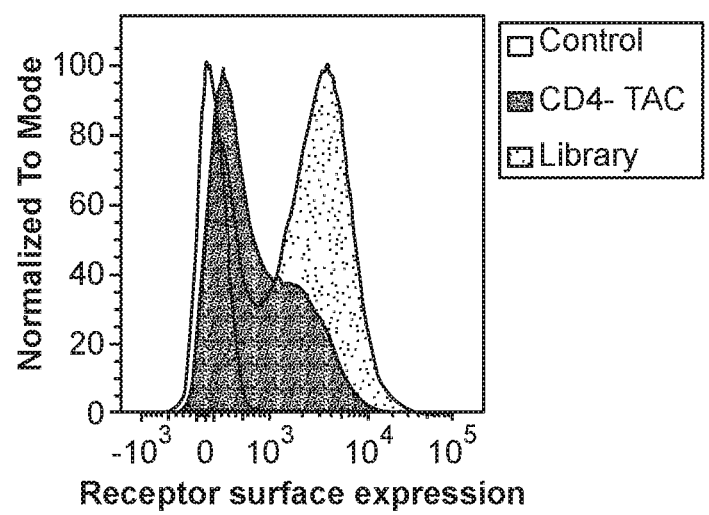

It is shown herein that UCHT1 mutant can be generated that results in enhanced surface expression of the TAG (FIGS. 15-17). Accordingly, in one embodiment, the TAG comprises a modified or mutated ligand that binds the TCR complex, wherein the TAG comprising the modified or mutated antibody has increased surface expression and/or activity compared to a TAG comprising a wild type, or non-modified or mutated ligand that binds the TCR complex. An example of a mutated or modified antibody that binds CD3 is the UCHT1 A85V, T161P mutant described herein (SEQ ID NO: 24 and 25).

Sequence Identity

The polynucleotides of the application also include nucleic acid molecules (or a fragment thereof) having at least about: 70% identity, at least 80% identity, at least 90% identity, at least 95% identity, at least 96% identity, at least 97% identity, at least 98% identity or, at least 99% or 99.5% identity to a nucleic acid molecule of the application. The polypeptides of the application also include polypeptides (or a fragment thereof) having at least about: 70% identity, at least 80% identity, at least 90% identity, at least 95% identity, at least 96% identity, at least 97% identity, at least 98% identity or, at least 99% or 99.5% identity to a polypeptide of the application. Identity refers to the similarity of two nucleotide or polypeptide sequences that are aligned so that the highest order match is obtained. Identity is calculated according to methods known in the art. For example, if a nucleotide sequence (called "Sequence A") has 90% identity to a portion of SEQ ID NO: 1, then Sequence A will be identical to the referenced portion of SEQ ID NO: 1 except that Sequence A may include up to 10 point mutations (such as substitutions with other nucleotides) per each 100 nucleotides of the referenced portion of SEQ ID NO:

Sequence identity is preferably set at least about: 70% identity, at least 80% identity, at least 90% identity, at least 95% identity, at least 96% identity, at least 97% identity, at least 98% identity or, most preferred, at least 99% or 99.5% identity to the nucleotide sequences provided herein and/or its complementary sequence. Sequence identity is also preferably set at least about: 70% identity, at least 80% identity, at least 90% identity, at least 95% identity, at least 96% identity, at least 97% identity, at least 98% identity or, most preferred, at least 99% or 99.5% identity to the polypeptide sequences provided herein. Sequence identity will preferably be calculated with the GCG program from Bioinformatics (University of Wisconsin). Other programs are also available to calculate sequence identity, such as the Clustal W program (preferably using default parameters; Thompson, J D et al., Nucleic Acid Res. 22:4673-4680).

Hybridization

The application includes DNA that has a sequence with sufficient identity to a nucleic acid molecule described in this application to hybridize under stringent hybridization conditions (hybridization techniques are well known in the art). The present application also includes nucleic acid molecules that hybridize to one or more of the sequences described herein and/or its complementary sequence. Such nucleic acid molecules preferably hybridize under high stringency conditions (see Sambrook et al. Molecular Cloning: A Laboratory Manual, Most Recent Edition, Cold Spring Harbor Laboratory Press, Cold Spring Harbor, N.Y.). High stringency washes have preferably have low salt (preferably about 0.2% SSC) and a temperature of about 50-65° C. and are optionally conducted for about 15 minutes.

Expression in T cells

The T cell antigen coupler is designed for expression in T cells. Accordingly, one aspect of the disclosure provides a T cell expressing a T cell antigen coupler. Another aspect of the disclosure relates to a T cell transduced or transfected with T cell antigen coupler or a vector comprising a T cell antigen coupler. Optionally, the T cell is an isolated T cell.

T cells can be obtained from a number of sources, including, but not limited to blood (for example, peripheral blood mononuclear cells), bone marrow, thymus tissue, lymph node tissue, cord blood, thymus tissue, tissue from an infection site, spleen tissue, and tumors. In one embodiment, the T cells are autologous T cells. In another embodiment, the T cells are obtained from a cell line of T cells. Methods of culturing and maintaining T cells in vitro are well known in the art.

Once obtained, the T cells are optionally enriched in vitro. As is well known in the art, a population of cells can be enriched by positive or negative selection. Further, the T cells can be optionally frozen or cryopreserved and then thawed at a later date.

Before or after introducing the T cell antigen coupler to the T cells, the T cells are optionally activated and/or expanded using methods well known in the art. For example, the T cells can be expanded by contact with a surface having attached thereto an agent that stimulates a CD3/TCR complex associated signal and a ligand that stimulates a co-stimulator molecule on the surface of the T cells.

Methods of transducing or transfecting T cells with nucleic acid sequences and expressing the transduced nucleic acids in the T cells are well known in the art. For example, a nucleic acid can be introduced into a cell by physical, chemical or biological means. Physical means include, but are not limited to, (microinjection, electroporation, particle bombardment, lipofection and calcium phosphate precipitation). Biological means include the use of DNA and RNA vectors.

In one embodiment, viral vectors, including retroviral vectors, are used to introduce and express a nucleic acid into a T cell. Viral vectors include vectors derived from lentivirus, Murine Stem Cell Viruses (MSCV), pox viruses, herpes simplex virus I adenovirus and adeno-associated viruses. The vector optionally includes a promoter that drives expression of the transduced nucleic acid molecule in a T cell.

Various assays may be used to confirm the presence and/or expression of the transduced nucleic acid sequence and/or the polypeptide encoded by the nucleic acid in the T cell. Assays include, but are not limited to Southern and Northern blotting, RT-PCR and PCR, ELISAs and Western blotting.

In one embodiment, a T cell expressing a T cell antigen coupler has increased T cell activation in the presence of an antigen compared to a T cell not expressing a T cell antigen coupler and/or as compared to a T cell expressing a traditional CAR. Increased T cell activation can be ascertained by numerous methods, including but not limited to, increased tumor cell line killing, increased cytokine production, increased cytolysis, increased degranulation and/or increased expression of activation markers such as CD107α, IFNγ, Il-2 or TNFα. Increases may be measured in an individual cell or in a population of cells.

The terms "increased" or "increasing" as used herein refer to at least a 2%, 5%, 10%, 25%, 50%, 100% or 200% increase in a T cell or population of T cells expressing a T cell antigen coupler compared to a T cell or population of T cells not expressing a T cell antigen coupler and/or as compared to a T cell or population of T cells expressing a traditional CAR.

T cells, optionally autologous T cells, expressing the T cell antigen coupler can be administered to a subject in need thereof. According, a T cell transduced with and/or expressing a T cell antigen coupler can be formulated in a pharmaceutical composition. Preferably, the T cells are formulated for intravenous administration.

A pharmaceutical composition can be prepared by per se known methods for the preparation of pharmaceutically acceptable compositions that can be administered to subjects, such that an effective quantity of the T cells are combined in a mixture with a pharmaceutically acceptable carrier. Suitable carriers are described, for example, in Remington's Pharmaceutical Sciences (Remington's Pharmaceutical Sciences, 20th ed., Mack Publishing Company, Easton, Pa., USA, 2000). On this basis, the compositions include, albeit not exclusively, solutions of the substances in association with one or more pharmaceutically acceptable carriers or diluents, and contained in buffered solutions with a suitable pH and iso-osmotic with the physiological fluids.

Suitable pharmaceutically acceptable carriers include essentially chemically inert and nontoxic compositions that do not interfere with the effectiveness of the biological activity of the pharmaceutical composition. Examples of suitable pharmaceutical carriers include, but are not limited to, water, saline solutions, glycerol solutions, ethanol, N-(1 (2,3-dioleyloxy)propyl)N,N,N-trimethylammonium chloride (DOTMA), diolesylphosphotidyl-ethanolamine (DOPE), and liposomes. Such compositions should contain a therapeutically effective amount of the compound, together with a suitable amount of carrier so as to provide the form for direct administration to the patient.

Pharmaceutical compositions may also include, without limitation, lyophilized powders or aqueous or non-aqueous sterile injectable solutions or suspensions, which may further contain antioxidants, buffers, bacteriostats and solutes that render the compositions substantially compatible with the tissues or the blood of an intended recipient. Other components that may be present in such compositions include water, surfactants (such as Tween), alcohols, polyols, glycerin and vegetable oils, for example. Extemporaneous injection solutions and suspensions may be prepared from sterile powders, granules, tablets, or concentrated solutions or suspensions.

(iii) Methods and Uses

One aspect of the present disclosure provides the use of a Trifunctional T-cell antigen coupler to direct a T cell to a specific antigen.

Accordingly, the present disclosure also relates to the use of a modified T cell for treating cancer in a subject in need thereof, wherein the modified T cell expresses a nucleic acid comprising a first polynucleotide encoding a target-specific ligand, a second polynucleotide encoding an ligand that binds the TCR complex; and a third polynucleotide encoding a T cell receptor signaling domain polypeptide. The disclosure also relates to methods for treating cancer, comprising administering an effective amount of modified T cells to a subject in need thereof. Also disclosed is use of an effective amount of modified T cells for treating cancer in a subject in need thereof. Further disclosed is use of a modified T cell in the preparation of a medicament treating cancer in a subject in need thereof. Even further disclosed is a modified T cell for use in treating cancer in a subject in need thereof. In one embodiment, the target-specific ligand binds an antigen on a cancerous cell, thereby targeting the modified T cell to the cancerous cell.

Cancers that may be treated include any form of neoplastic disease. Examples of cancers that may be treated include, but are not limited to breast cancer, lung cancer and leukemia, for example mixed lineage leukemia (MLL), chronic lymphocytic leukemia (CLL) or acute lymphoblastic leukemia (ALL). Other cancers include carcinomas, blastomas, melonomas, sarcomas, hematological cancers, lymphoid malignancies, benign and malignant tumors, and malignancies. The cancer can comprise non-solid tumors or solid tumors. Cancers that may be treated include tumors that are not vascularized, or not yet substantially vascularized, as well as vascularized tumors.

The modified T cells and/or pharmaceutical compositions described herein may be administered to, or used in, living organisms including humans, and animals. The term "subject" as used herein refers to any member of the animal kingdom, preferably a mammal, more preferably a human being.

Procedures for isolating, genetically modifying, and administering T cells to a subject in need thereof are known in the art. In particular, T cells are isolated from a mammal (preferably a human), optionally expanded and/or activated as described herein and transduced or transfected with the nucleic acid molecules of the disclosure. The T cells can be autologous with respect to the subject. In another embodiment, the cells can be allogeneic, syngeneic or xenogeneic with respect to the subject.

The modified T cells can be administered either alone, or as a pharmaceutical composition, as described herein. Compositions of the present disclosure are preferably formulated for intravenous administration.

Administration of an "effective amount" of the modified T cells and/or pharmaceutical compositions is defined as an amount effective, at dosages and' for periods of time necessary to achieve the desired result. For example, an effective amount of a substance may vary according to factors such as the disease state, age, sex, and weight of the individual, and the ability of the recombinant protein to elicit a desired response in the individual. Dosage regime may be adjusted to provide the optimum therapeutic response. For example, several divided doses may be administered daily or the dose may be proportionally reduced as indicated by the exigencies of the therapeutic situation.

For example, the modified T cells and/or pharmaceutical compositions described herein may be administered at a dosage of $10^4$ to $10^9$ cells per kg body weight, optionally $10^5$ to $10^8$ cells per kg body weight or $10^6$ to $10^7$ cells per kg body weight. The dosage can be administered a single time or multiple times.

The modified T cells and/or pharmaceutical compositions may be administered by any method known in the art, including but not limited to, aerosol inhalation, injection, ingestion, transfusion, implantation or transplantation. The modified T cells and/or pharmaceutical compositions may administered to a subject subcutaneously, intradennally, intratumorally, intranodally, intrameduliary, intramuscularly, by intravenous (i.v.) injection, or intraperitoneally. The modified T cells and/or pharmaceutical compositions thereof may be injected directly into a tumor, lymph node, or site of infection.

As used herein, and as well understood in the art, "to treat" or "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. In one embodiment, "treatment" includes preventing a disease or condition.

| SEQ ID NO | Description | Nucleotide/Amino Acid |
|---|---|---|
| SEQ ID NO: 1 | N-Darpin Tri TAC | Nucleotide |
| SEQ ID NO: 2 | N-Darpin Tri TAC | Amino Acid |
| SEQ ID NO: 3 | C-Darpin Tri TAC | Nucleotide |
| SEQ ID NO: 4 | C-Darpin Tri TAC | Amino Acid |
| SEQ ID NO: 5 | N-Darpin Tri TAC leader sequence (secretion signal) | Nucleotide |
| SEQ ID NO: 6 | N-Darpin Tri TAC leader sequence (secretion signal) | Amino Acid |
| SEQ ID NO: 7 | DARPin specific for Her2 antigen | Nucleotide |
| SEQ ID NO: 8 | DARPin specific for Her2 antigen | Amino Acid |
| SEQ ID NO: 9 | Myc Tag | Nucleotide |
| SEQ ID NO: 10 | Myc Tag | Amino Acid |
| SEQ ID NO: 11 | Linker 1 | Nucleotide |
| SEQ ID NO: 12 | Linker 1 | Amino Acid |
| SEQ ID NO: 13 | UCHT1[1] | Nucleotide |
| SEQ ID NO: 14 | UCHT1[2] | Amino Acid |
| SEQ ID NO: 15 | Linker 2 | Nucleotide |
| SEQ ID NO: 16 | Linker 2 | Amino Acid |
| SEQ ID NO: 17 | CD4 Domain[3] | Nucleotide |
| SEQ ID NO: 18 | CD4 Domain[4] | Amino Acid |
| SEQ ID NO: 19 | Universal rigid linker | Amino Acid |
| SEQ ID NO: 20 | CD28 based linker | Amino Acid |
| SEQ ID NO: 21 | CD4 based linker | Amino Acid |
| SEQ ID NO: 22 | ScFv specific for Her2 antigen | Nucleotide |
| SEQ ID NO: 23 | ScFv specific for Her2 antigen | Amino Acid |
| SEQ ID NO: 24 | UCHT1 (A85V, T161P) | Nucleotide |
| SEQ ID NO: 25 | UCHT1 (A85V, T161P) | Amino Acid |

[1]Light chain, nucleotides 1-324; Linker, nucleotides 325-387; Heavy chain, nucleotides 388-750
[2]Light chain, amino acids 1-108; Linker, amino acids 109-128; Heavy chain, amino acids 129-250
[3]Extracellular linker, nucleotides 1-66; Transmembrane domain, nucleotides 67-132; Cytosolic domain, nucleotides 133-254
[4]Extracellular linker, amino acids 1-22; Transmembrane domain, amino acids 23-44; Cytosolic domain, amino acids 45-84

The above disclosure generally describes the present application. A more complete understanding can be obtained by reference to the following specific examples. These examples are described solely for the purpose of illustration and are not intended to limit the scope of the application. Changes in form and substitution of equivalents are contemplated as circumstances might suggest or render expedient. Although specific terms have been employed herein, such terms are intended in a descriptive sense and not for purposes of limitation.

The following non-limiting examples are illustrative of the present application.

EXAMPLES

Example 1

Background and Summary

A trifunctional T cell-antigen coupler (Tri-TAC) was developed to better recapitulate the natural signaling through the TCR, while retaining MHC unrestricted targeting. T-cell activation occurs following ligation of MHC by the TCR and co-receptor on the T cells (either CD4 or CD8) simultaneously bind to conserved regions within the MHC molecule (Yin et al., 2012)(Kuhns and Davis, 2012). The co-receptors are specifically located within "lipid rafts" (Fragoso et al., 2003XArcaro et al., 2000), membrane micro domains that are particularly important for TCR signal complex formation (He and Marguet, 2008). In addition to ensuring the correct microdomain localization of the TCR activation complex, these co-receptors also bind directly to Lck (Kim et al., 2003), a protein kinase that is crucial for T-cell activation (Methi et al., 2005)(Acuto and Cantrell, 2000). As stated previously, none of the existing chimeric receptors or bi-functional proteins engage the co-receptor molecules or Lck. A molecule was created where the transmembrane and intracellular regions of the CD4 co-receptor, which localize to the lipid raft and bind Lck, respectively, were fused to single-chain antibody that binds CD3 (UCHT1; SEQ ID NO: 13 and 14; sequence is also in the public domain). This construct is designed to draw the CD3 molecule and the TCR into regions of lipid rafts and bring Lck into the proximity of the TCR, similar to natural MHC binding. To target this chimeric receptor, a designed ankyrin repeat (DARPin) was linked to the CD4-UCHT1 chimera to generate a tri-functional T cell-antigen coupler (Tri-TAC). In this specific case, the DARPin was specific for the proto-oncogene, erbB-2.

Human T cells were engineered to express either the prototype Tri-TAC or a conventional CAR with the same DARPin. It was determined that in all aspects, T cells engineered with the Tri-TAC demonstrated functionality equivalent to a conventional CAR. Interestingly, with regard to 2 parameters (TNF-α production and CD107a mobilization), it was observed that the Tri-TAC was more active than a conventional CAR. Further, the data shows that on a per molecule basis the Tri-TAC shows a significantly enhanced activity. Additionally the Tri-TAC offers enhanced safety compared to traditional CARs as no activation domains are part of the protein.

The traditional CAR is effective in stimulating T-cells by combining several signaling domains (FIG. 1C). By comparison, the Tri-TAC (FIG. 1 A/B) does not contain any signaling domains of its own. It relies purely on facilitating the proposed interactions between other key players (shown in grey) in an antigen dependent manner. To test this design hypothesis, several variants of the full length N-Darpin Tri-TAC were generated (FIG. 1D).

Previous work has established the consistent and significant cell surface expression of CAR molecules. It was found that the Darpin CAR shows robust surface expression (FIG. 2). In contrast, Tri-TAC showed a much lower surface expression. This was observed for all variants that had the UCHT1 domain. However, the Tri-TAC variant lacking the UCHT1 domain showed surface expression similar to the Darpin CAR.

Figures 3A, 3B:
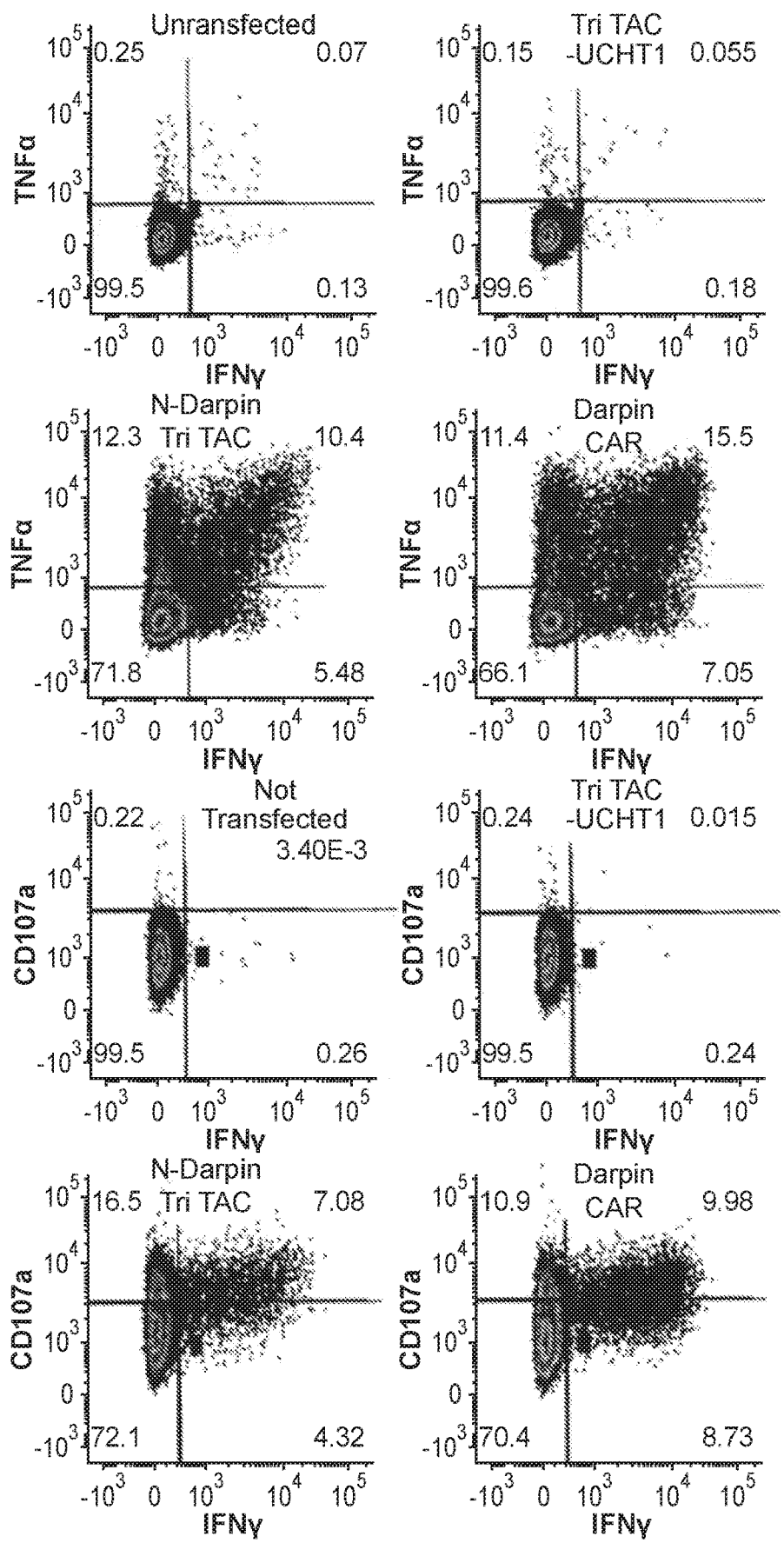

T cells engineered to express the Tri-TAC, the Tri-TAC variants or The T cells the DARPin CAR were stimulated with plate-bound antigen, engineered to express the Tri-TAC and DARPin CAR could elaborate all measured functions (TNF-α production, IFN-γ production and CD107a mobilization) (FIGS. 3A and 3B). Binding of the Tri-TAC to both CD3 and the target antigen was found to be critical for the T cells to elaborate their functions. In FIG. 3, it is demonstrated that removal of UCHT1, which abolishes binding to CD3, abrogates the function of the Tri-TAC. In other data, it was determined that removal of the DARPin from the Tri-TAC also abrogates function.

Figure 4:
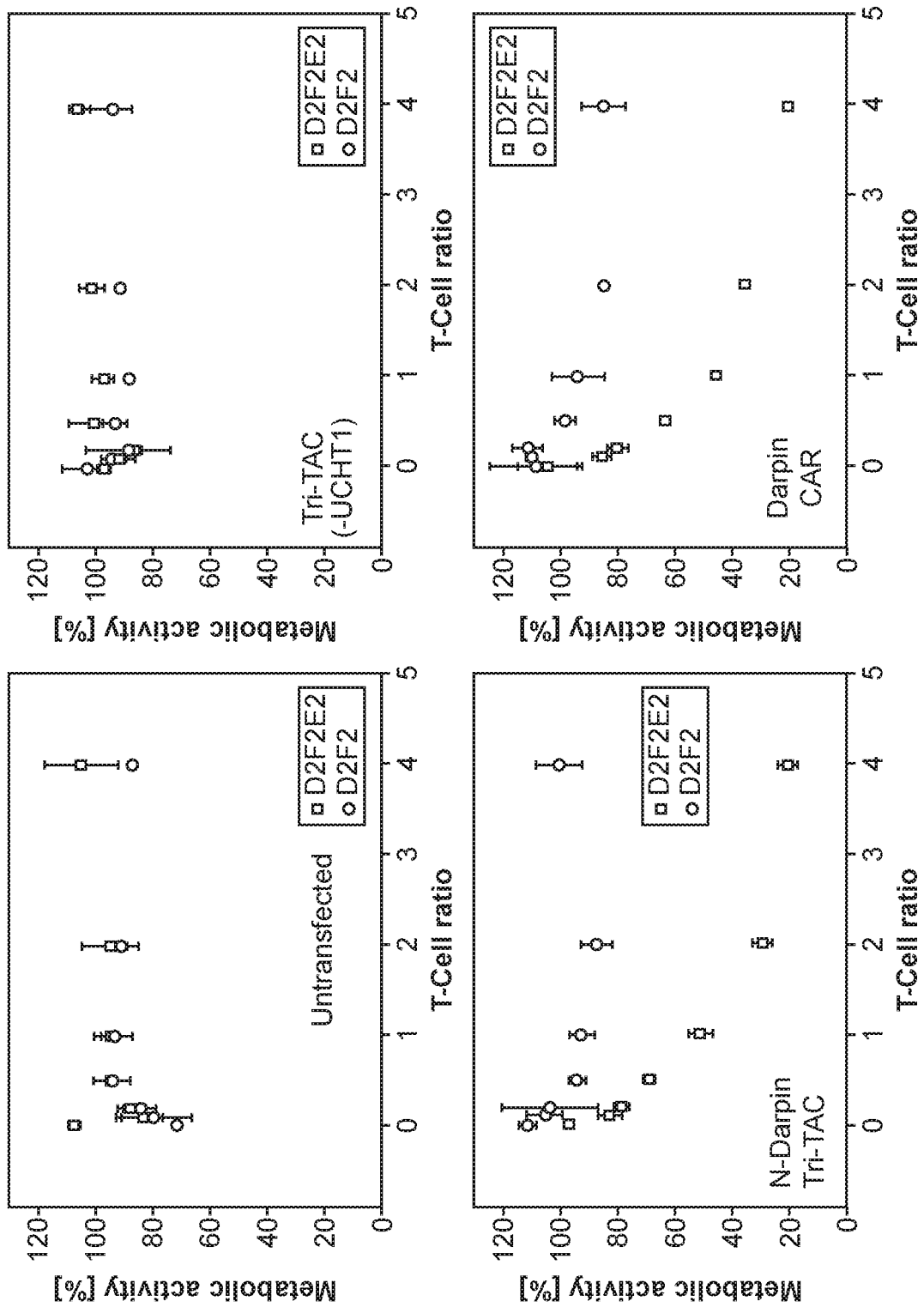
FIG. 4 analyzes the killing of two different cell lines that either express (D2F2E2) or do not express (D2F2) the molecular target of the classical CAR and the Tri-TAC.

As expected, when these T-cells were tested for their cytotoxicity, Tri-TAC-UCHT1-Darpin showed no ability to kill antigen expressing cells (FIG. 4). N-Darpin Tri-TAC showed a high level of selective cytotoxicity that was very similar to the classical DARPin-CAR. Interestingly, the T cells expressing the DARPin-CAR appear to display off-target killing at high T-cell:target cell ratios (see killing on D2F2 in FIG. 4) whereas the T cells expressing the Tri-TAC did not display these effects.

EXPERIMENTAL

FIG. 1 is a schematic overview. (A) Depicts N-Darpin Tri-TAC. The ankyrin repeat domain targeted against Her2 is fused to the single chain fragment variable (scFv) UCHT1 using a $(G4S)_3$ linker. The scFv is then linked to the CD4 molecule. The CD4 contains the linker region and transmembrane region as well as the cytoplasmic anchoring region. Potential interactions are shown in faded gray. (B) Depicts the C-Darpin Tri-TAC. In this construct, the scFv UCHT1 is switched with the Darpin domain. Potential interactions are again depicted in faded gray. (C) Model of a classical second generation CAR. The Darpin targeting domain is linked via a CD8a linker to the CD28 transmembrane domain. The CD3 zeta domain with its 3 activating ITAM motifs is then connected to the cytosolic portion of CD28. (D) Overview of the various Tri-TAC controls, lacking either the Darpin targeting domain, the CD3 binding scFv moiety, or the cytosolic portion of the CD4 domain.

FIG. 2 shows the phenotypic surface expression analysis of transduced T-cells with histograms of respective Tri-TAC variants. T-cells had been incubated with Her2Fc, which later was detected via flow cytometry. The presented data was gated on CD8+ lymphocytes. The shown gates were chosen based on the untransduced control.

FIG. 3 is a functional analysis of engineered T-cells. In (A), cells were stimulated for 4 hours with plate bound Her2Fc in media containing GolgiPlug™. Cells were first stained for CD8+, then permeabilized and analyzed for TNF-α and IFN-γ production. Initial gates were set for singlet CD8+ lymphocytes. The shown gates were set based on the untransduced control. In B), as before, cells were stimulated with plate bound Her2Fc. Media included GolgiPlug™ as well as an anti-CD107a antibody. Actively degranulating cells were expected to have a higher rate of CD107a recycling, and subsequently show a higher signal for anti-CD107α.

FIG. 4 shows engineered T-cell cytotoxicity. Two different adherent mouse tumor lines were plated 24 hours prior to T-cell addition. D2F2/E2 have been engineered to express human Her2, whereas the D2F2 do not. Indicated ratios of T-cells were added to tumor containing wells. Tumor cells were incubated for 6h with T-cells. T-cells were subsequently removed via washing. 10% Alamar blue containing media was added to each well for 3 hours. The metabolic activity, as an indicator of cell survival, was determined via endpoint analysis. Wells without T-cells were defined as maximum survivability/metabolic activity and set to 100%, whereas media incubated without cells was set as 0% metabolic activity. Data presented is the average of 3 replicates.

DISCUSSION

Using chimeric receptors to redirect T-cells towards specific targets in an MHC-independent manner is an attractive method to treat cancer and may be applicable to infectious diseases where antigens from the pathogen are found on the plasma membrane. The chimeric receptor would result in: (1) specific cytotoxicity against the target cells and (2) minimal off target toxicity. Conventional CARs are limited in this regard because they rely upon a synthetic structure where signaling domains are located in unnatural positions where they may not receive proper regulation and, thus, there is reduced cellular control of specific activity.

The Tri-TAC was designed to re-direct the signaling components of the natural TCR without employing ectopic localization of signaling domains. The Tri-TAC was designed with the following principles: (1) the chimeric receptor should interact and facilitate ordered assembly of key activating protein complexes, (2) the chimeric receptor should take advantage of preexisting cellular adaptations, such as micro-domain environments and (3) the chimeric receptor should not possess any activating domains. The Tri-TAC is able to achieve this efficiently and, as the data demonstrates, at rates of activation that are equal to, if not better than, that of a 2nd generation CAR.

This Tri-TAC is thus ideally suited for further integration with additional designed co-receptors to further fine tune T-cell activation. Ultimately this should lead to much reduced off target effects without compromising on targeted cytotoxicity. Tri-TAC appears to exhibit lower toxicity than existing CARs. Darpin CARs show mild off target killing at high cell to target ratios, which may become problematic when used in therapies. However, Tri-TAC, which is as functional as the traditional CAR, did not display off-target effects. Since DARPins bind targets with high affinity, off-target effects may be more common on cells that express high levels of a chimeric receptor that employs a DARPin. Therefore, without being bound by theory, the low surface expression of the Tri-TAC may be advantageous as it reduces the likelihood of such off-target effects.

Ultimately, the modular nature of the Tri-TAC technology allows much more sophisticated fine tuning of the T-cell activation process. For example, the recruitment of the TCR complex could be modulated by engineering Tri-TAC molecules with a lower CD3 affinity. This could be used to mimic the natural low TCR affinity (Chervin et al., 2009) while retaining a high affinity targeting domain to detect cancer targets. Unlike the classical CAR, the Tri-TAC technology can be engineered to more closely resemble this.

In conclusion, the presented Tri-TAC technology is a highly efficient molecular tool that is able to (1) efficiently trigger T-cell activation and cytotoxicity, (2) is able to do this by mimicking natural T-cell activation and (3) does not require activation domains of its own.

Example 2. Characterization of the Tri-TAC Technology

An overview of the Tri-TAC technology is provided in FIG. 5.

Figure 5C:
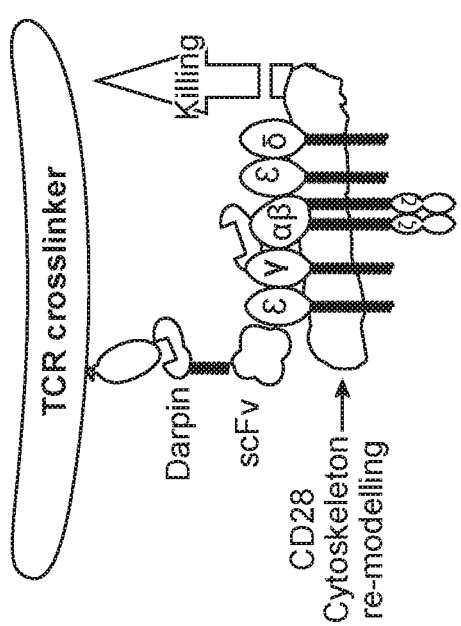
FIGS. 5A-D depict natural T-cell initiation (5A), two currently used artificial methods for T-cell activation (5B and 5C), and the TAC activation technology (5D).
Figure 5D:
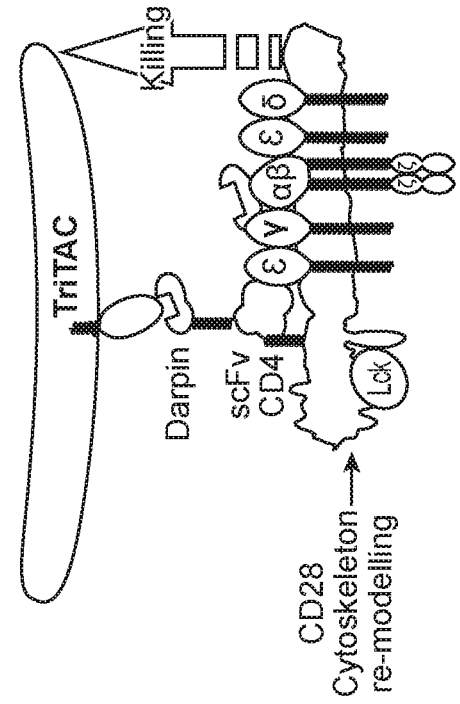
Figure 5A:
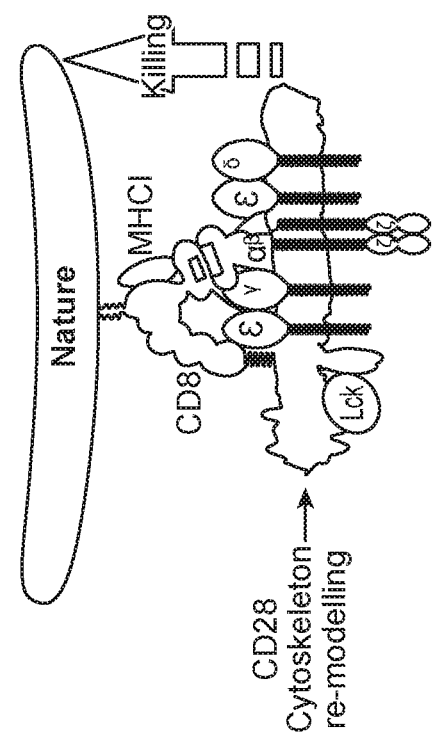

FIG. 5A shows an example of CD8 T-cell activation based on the co-assembly of different receptors and their associated protein partners. Initially, the major histocompatibility complex I is presenting an antigen (helix). This is recognized by a T cell receptor (TCR) complex capable of binding the antigen. The TCR complex contains several individual subunits. The α/β domains are able to interact directly with the antigen presented on MHC-I. The α/β domains then interact with several other domains (ε, γ, δ, and ζ all of which participate in T-cell activation via various intracellular activation domains. The TCR complex interacts with MHC-I concurrently with the CD8 co-receptor. The CD8 co-receptor binds to the MHC-I in an antigen independent manner. CD8 directly interacts with Lck, a protein kinase important for activating the TCR receptor complex. The CD8 and Lck interaction also ensures their association with lipid rafts (membrane portion) microdomains, which are hypothesised to organize and encapsulate other relevant signalling moieties (dark spheres). Later stages of activation then lead to CD28 recruitment. If this interaction cascade occurs several times in parallel, T-cells become activated and are able to exert their cytotoxic effects.

Figure 5B:
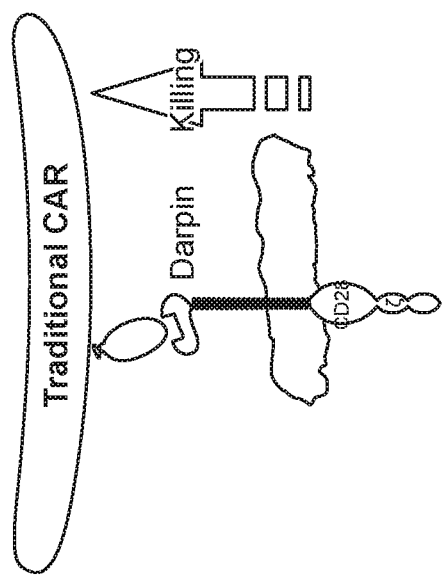

FIG. 5B provides an overview of Chimeric Antigen Receptors (CAR). CARs seek to reproduce the complex mechanism of T-cell activation by combining several key activation domains, such as ζ and CD28, in a single synthetically engineered molecule. The CAR then directly interacts with an antigen of choice using specific binding domains. Depicted here is an ankyrin repeat protein (DARPin). It is believed that several such interactions occurring in parallel lead to T-cell activation.

FIG. 5C depicts bispecific T-cell engager (BiTE) like molecules which engage T-cells by directly cross linking the TCR complex to an antigen of choice. The BiTE like molecule depicted here contains two binding domains. The DARPin moiety is interacts with the target antigen. The single chain variable fragment domain (scFv) binds the TCR complex via its epsilon domain. Several such crosslinkings occurring in parallel lead to T-cell activation.

FIG. 5D is an overview of the TAC technology mimicking the natural activation process. The T-cell Antigen Coupler (TAC) is able to bind to its antigen via the DARPin binding domain. DARPin is then linked to a scFv able to bind the epsilon domain of the TCR complex. The TAC then associates with the CD4 transmembrane and cytosolic domain. CD4, like CD8, interacts with Lck and is situated in lipid rafts. Thus, TACs combine TCR recruitment with co-receptor stimulation. Without being bound by theory, it is believed that several such interactions happening in parallel lead to T-cell activation.

Figure 6B:
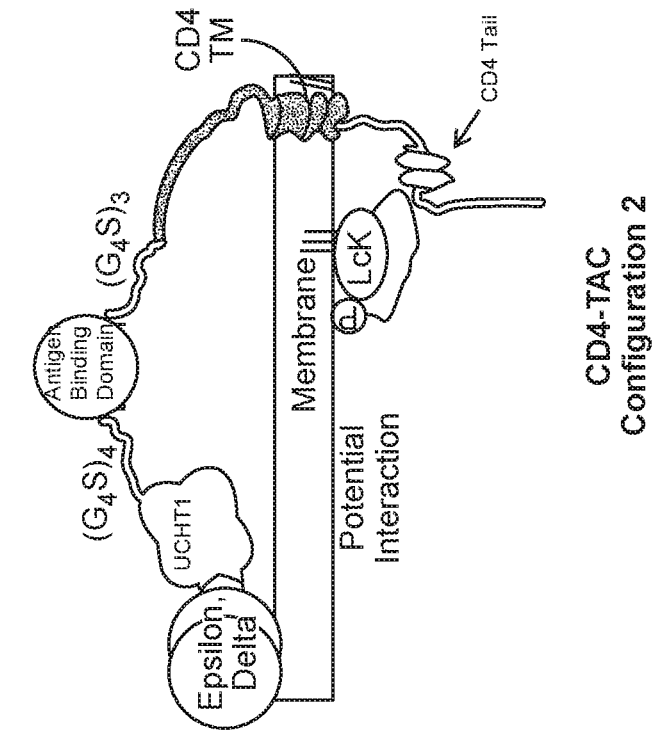
FIGS. 6A-B depicts (6A) configuration 1 of the TAC molecule and (6B) configuration 2 of the TAC molecule.
Figure 6A:
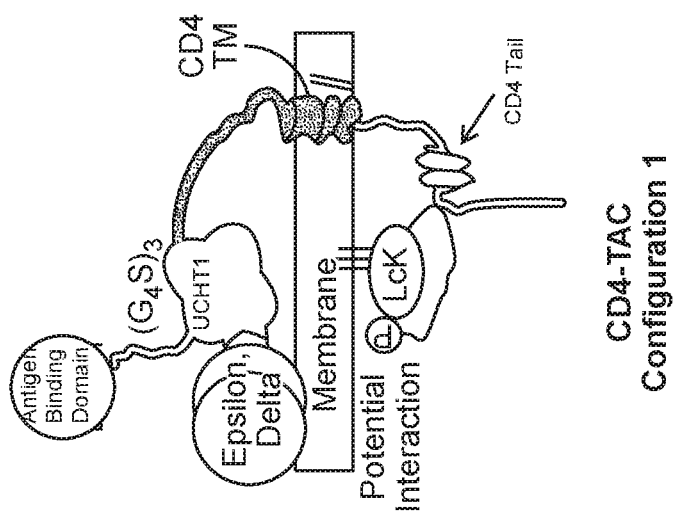
Figure 8A:
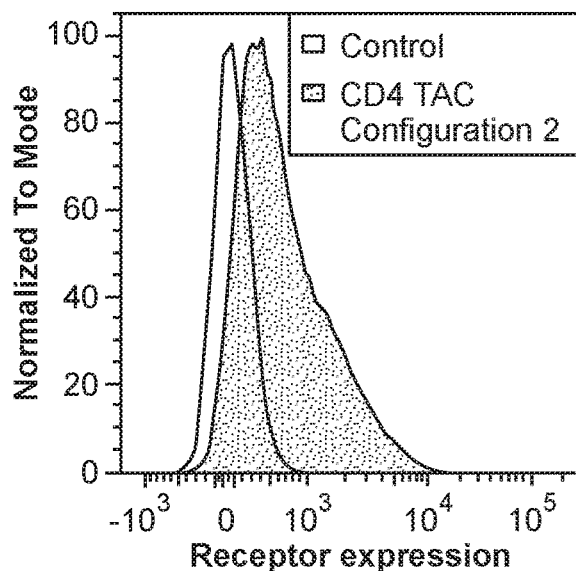
FIGS. 8A-C characterize the CD4-TAC configuration 2. (8A) is a histogram showing surface expression of the DARPin CD4 TAC receptor relative to empty vector, (8B) shows cytokine production and degranulation of T cell engineered with DARPin TAC configuration 2 exposed to Her2 antigen and (8C) shows growth of CD4 TAC configuration 2 relative to empty vector control.
Figure 8A:
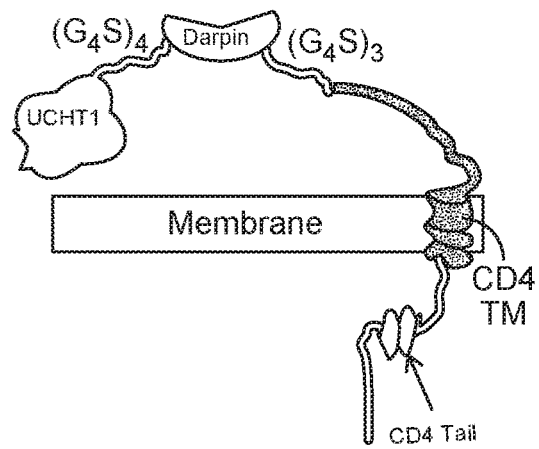
Figure 8B:
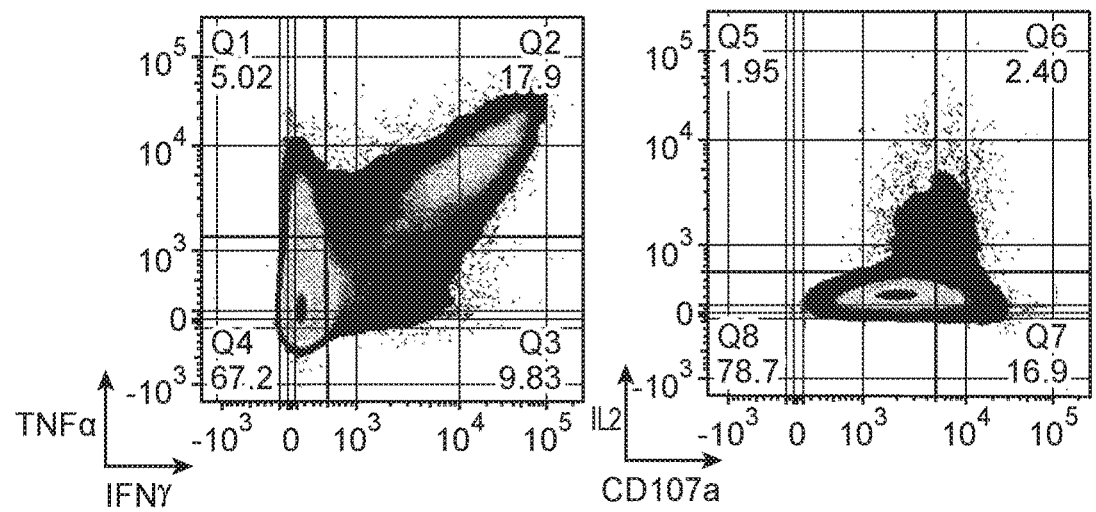
Figure 8C:
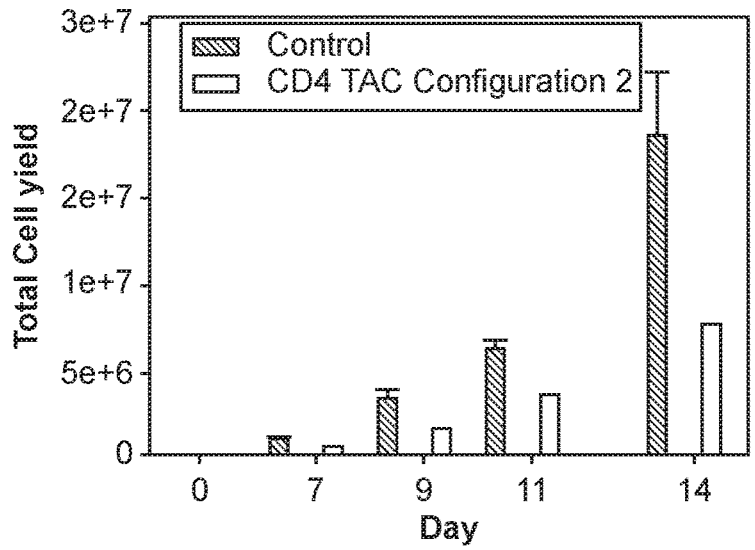
Figure 9A:
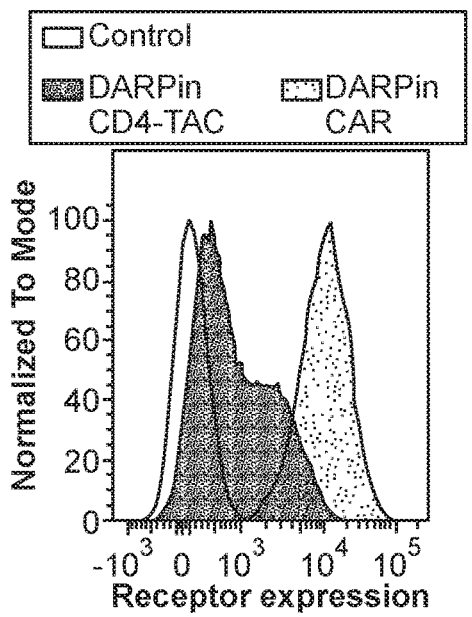
FIGS. 9A-D shows the functionality of DARPin CD4 TAC configuration 1. (9A) shows the surface expression of DARPin CD4 YAC compared to DARPin CAR and the NGFR only control, (9B) shows growth of CD4 TAC configuration 1 and (9C) and (9D) show the percentage of cells positive for various activation and degradation markers.
Figure 9B:
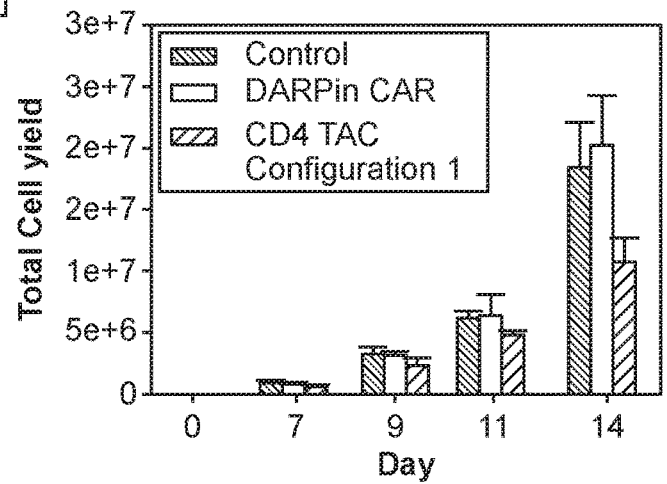
Figure 9C:
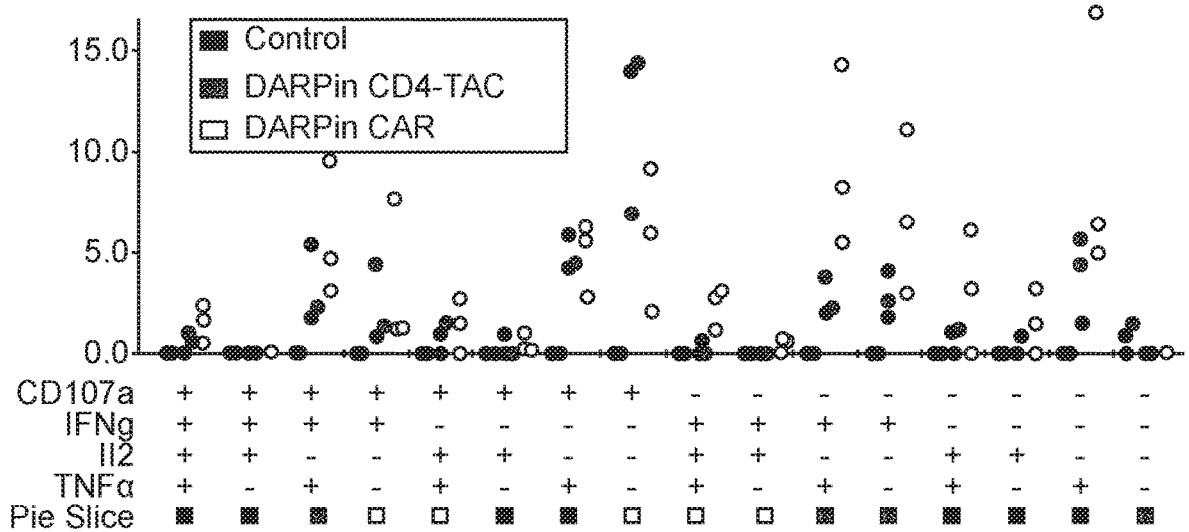
Figure 9D:
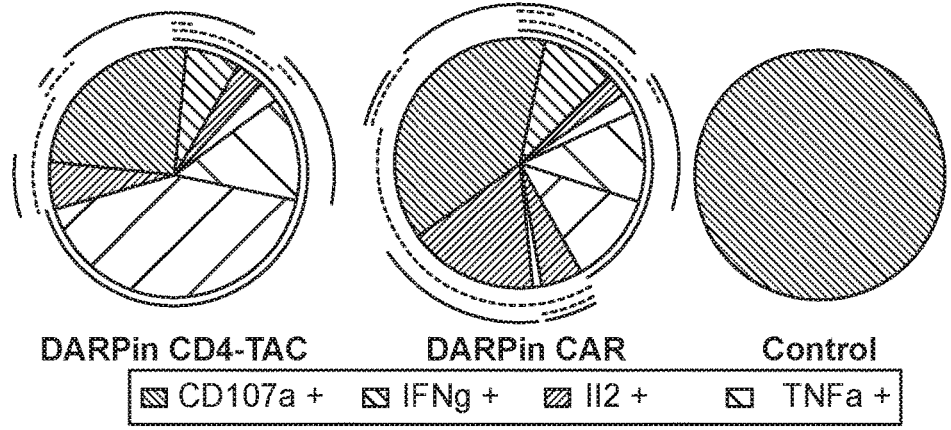

Different configurations of the TAC molecule are possible. FIG. 6A shows a model of the TAC molecule in configuration 1. The CD4-tail, 5 transmembrane, and linker domains are combined with the TCR-epsilon specific scFv (UCHT1). The scFv is then linked to the antigen binding domain. This domain is exchangeable. In this proposal the antigen binding domains used are either a scFv or DARPin domain specific for the Her2 antigen. FIG. 6B shows a TAC molecule in configuration 2. Here, the CD4 domains first interact with the antigen binding domain. This domain is then linked to the TCR recruiting scFv (UCHT1) domain.

FIG. 7 shows the functionality of scFv CD4 TAC. FIG. 7A is a histogram showing surface expression of the scFv CD4 TAC receptor relative to empty vector. Cells were stained using an FcHer2 antigen, which was in turn detected using fluorescently labelled antibodies. FIG. 7B shows antigen specific activation of T-cells expressing either the scFv CD4 TAC (top) or scFV CAR (bottom). T-cells expressing either the scFv CD4 TAC (top) or scFv CAR (bottom) were incubated with plate bound Her2 antigen. Both modified cells showed antigen specific activation. The DMSO negative control showed no activity (Data not shown). FIG. 7C shows comparable killing of MCF-7 human tumour cell line (Her2 positive) by both scFv CD4 TAC and scFv CAR. Both scFv CD4 TAC and scFv CAR were incubated with MCF-7 human tumour cell line (Her2 positive) and compared to an empty vector control.

FIG. 8 is a characterization of CD4-TAC configuration 2. FIG. 8A is a histogram of DARPin CD4-TAC configuration 2 relative to vector control. Surface expression was probed with the FcHer2 modified antigen. Cells expressing CD4-TAC configuration 2 show a distinct increase in FcHer2 binding demonstrating high surface expression of the receptor. For clarity the model of CD4 TAC configuration 2 is shown. FIG. 8B shows T-cells engineered with DARPin TAC configuration 2 exposed to plate bound Her2 antigen. Cytokine production and degranulation were measured. Data show that DARPin TAC configuration 2 is a functional receptor. Treatment without antigen showed no T-cell activation (data not shown). FIG. 8C shows growth of CD4 TAC configuration 2 relative to empty vector control. Cells were grown in 100u/ml IL2 10 ng/ml IL7. Starting with 100,000 cells, growth was monitored by counting culture samples at predetermined intervals. Configuration 2 has a marked reduced growth rate relative to control.

FIG. 9 shows the functionality of DARPin CD4 TAC configuration 1. FIG. 9A shows surface expression of DARPin CD4 TAC (red) compared to DARPin CAR (green), and the NGFR only control (blue). Cells were probed with receptor specific antigen FcHer2. Histogram shows that DARPin CD4 TAC is expressed well on the surface. However, its maximal surface expression is lower compared to the CAR construct. FIG. 9B shows growth of CD4 TAC configuration 1. For two weeks culture growth was monitored by sampling and manually counting cells. The empty vector shows similar growth as DARPin CAR. However TAC has reduced growth by comparison. FIGS. 9C and 9D show the percentage of cells positive for various activation and degradation markers. Empty vector, DARPin CD4 and DARPin CAR were incubated with either plate bound antigen Her2 or DMSO control. The results of three separate experiments are summarized using the statistical analysis software SPICE. The scatter graph shows the percentage of cells positive for a set of activation markers. CD4-TAC show a higher percentage of cells, positive for degranulation markers. DARPin CAR cells are positive for a variety of activation markers with no significantly enriched population of degranulation markers. The pie chart represents the same data. It demonstrates that CD4-TAC has a markedly higher population of cells focused on degranulation. CD4-TAC has a majority of activated cells degranulate with various levels of cytokine production. However, CARs show a more randomly distributed pattern of activation with degranulation constituting less than 50% of the total population. The pattern may be indicative of a less controlled T-cell activation by CARs.

Figure 10:
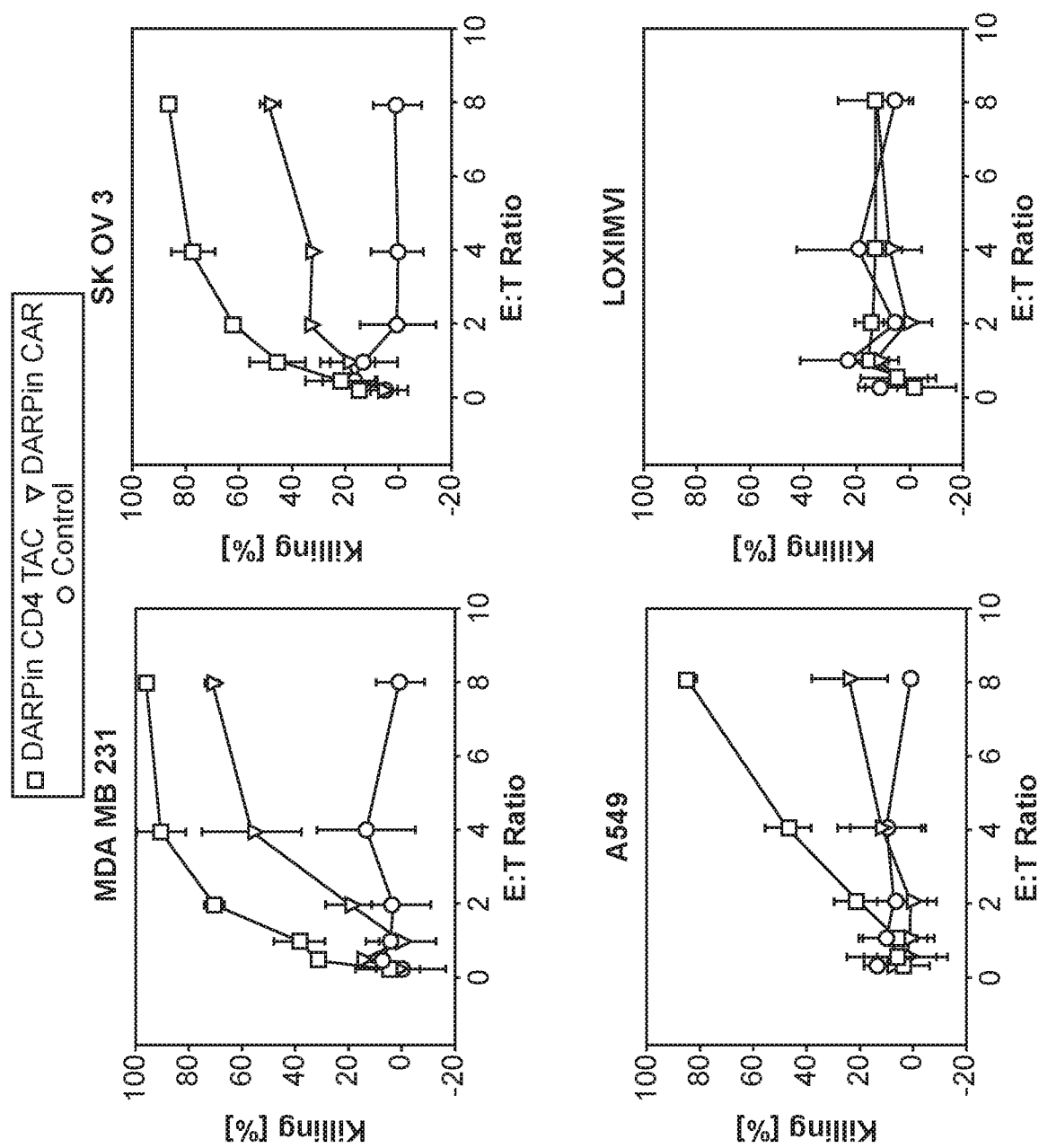
FIG. 10 shows the cytotoxicity and overall activity of TAC and CAR. Cells engineered with TAC, CAR or empty vector control were incubated in various human tumor cell lines.

FIG. 10 shows cytotoxicity and overall activity of TAC and CAR. Cells engineered with either TAC, CAR or empty vector control were incubated with various human tumour cell lines. MDA MB 231, SK OV 3 and A549 all express the Her2 antigen. LOXIMVI is Her2 negative. It was observed that in all cases, TAC shows enhanced cytotoxicity. The antigen negative cell line LOCIMVI is not being targeted, supporting that cytotoxicity is antigen specific.

Figure 11A:
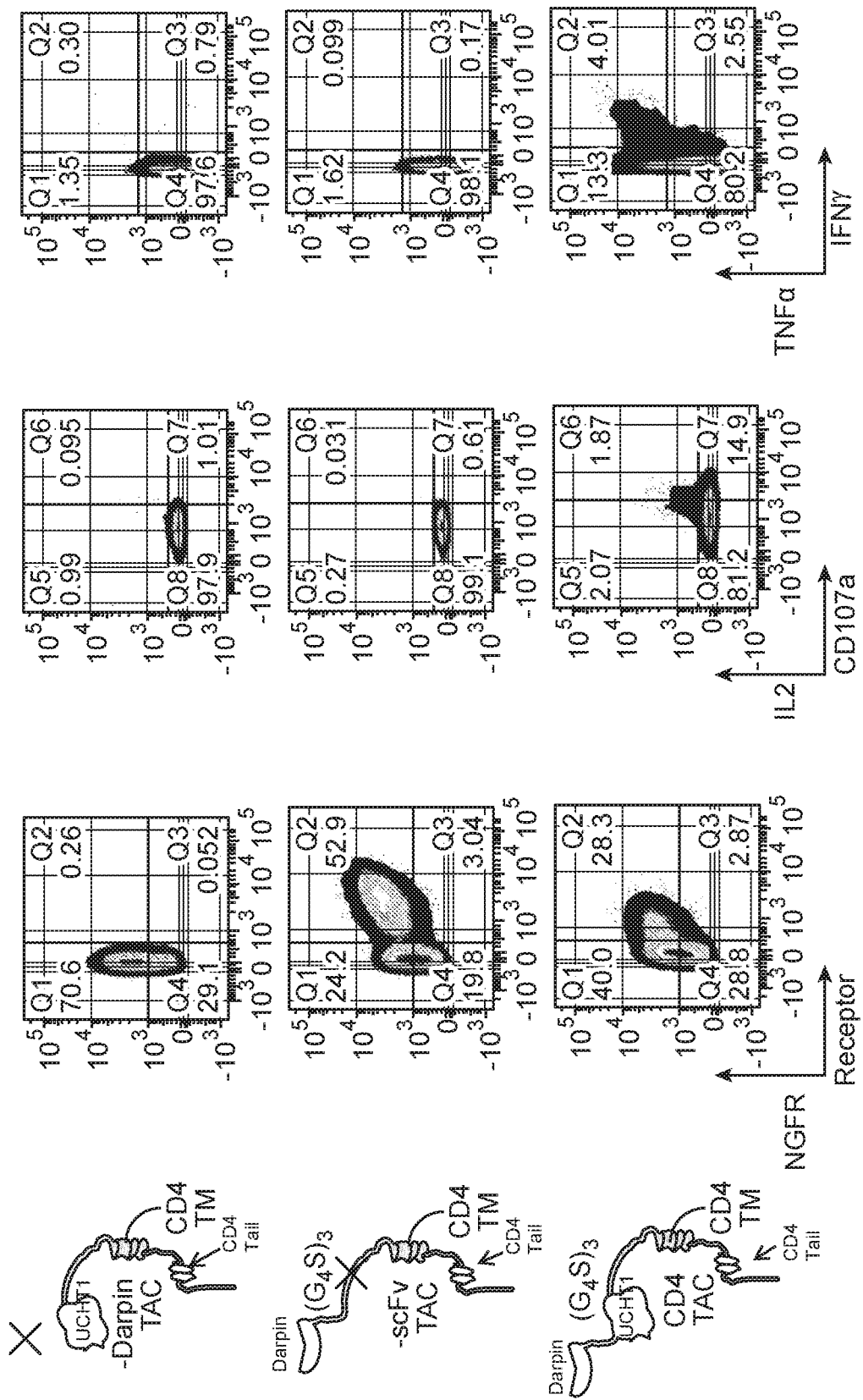
FIGS. 11A-B show receptor surface expression and activation of various TAC controls. (11A) shows cell surface expression (left), degranulation (middle) and cytokine production (right) and (11B) shows that only full length CD4-TAC is able to elicit a cytotoxic response.
Figure 11B:
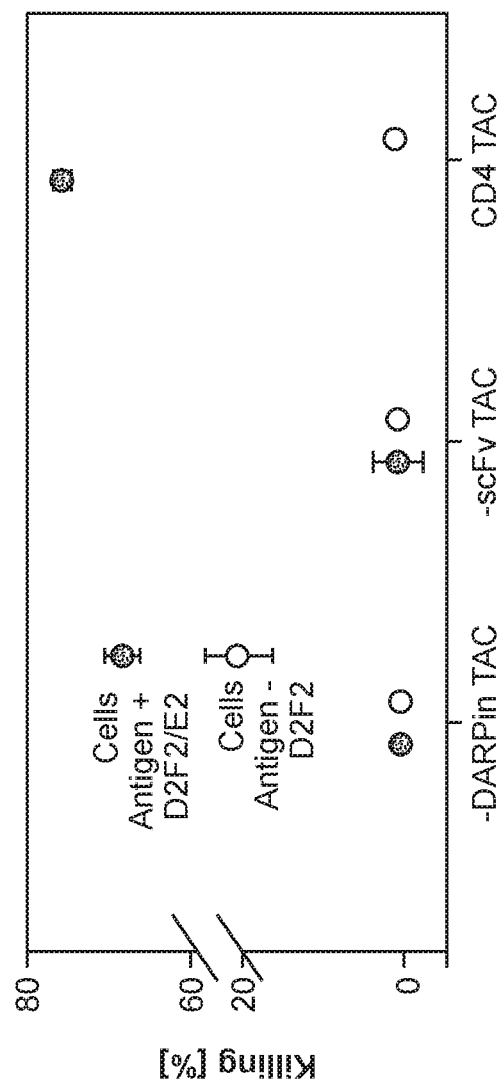

FIG. 11 shows receptor surface expression and activation of various TAC controls. Cell surface expression (left), degranulation (middle) and cytokine production (right) is shown in FIG. 11A. Constructs lacking specific domains were made to determine the significance of these domains. From top to bottom the following domains were removed: DARPin antigen binding domain and UCHT1 TCR binding domain, with the full length TAC being at the bottom. Surface expression of TAC without the UCHT1 domain resulted in enhanced surface expression relative to full length CD4 TAC. The DARPin negative mutant could not be detected using FcHer2 antigen. Degranulation (middle) was only observed in full length TAC. Both UCHT1 and DARPin deletion resulted in no degranulation. Similarly, cytokine production was only observed in the full length TAC. FIG. 11B shows the mouse cell line D2F2 was engineered to express the human Her2 antigen (D2F2/E2). Both cell lines were incubated with T-cells engineered with full length CD4-TAC or its deletion variants. The data show the Effector to Target ratio 4:1 endpoint. Only full length CD4-TAC was able to elicit a cytotoxic response. This demonstrates that DARPin and UCHT1 domains are involved in receptor function.

Figure 12A:
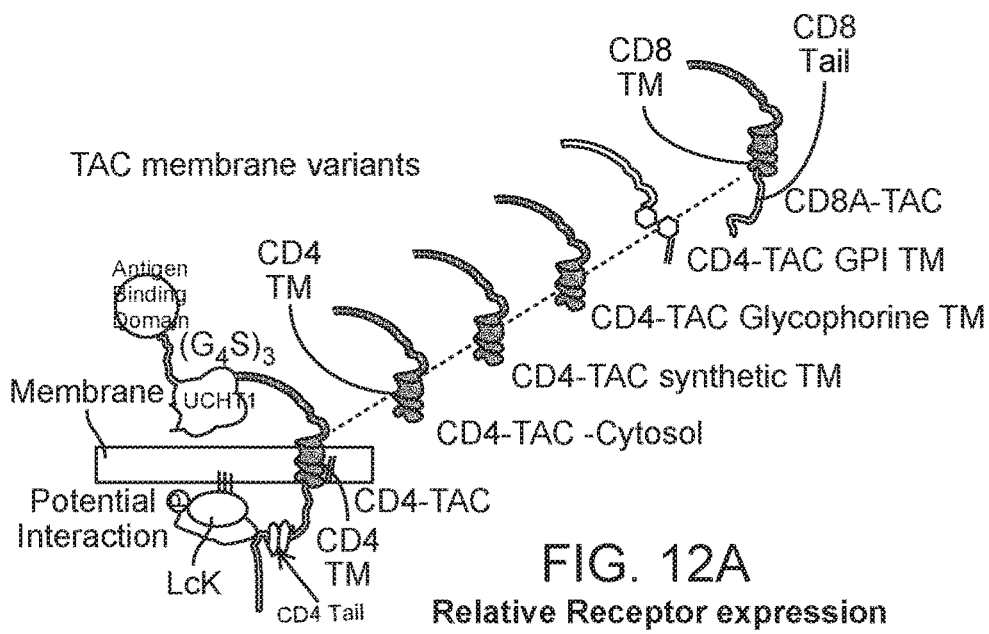
FIGS. 12A-C show properties of various transmembrane TAC variants. (12A) is an overview of various transmembrane domain constructs, (12B) shows the surface of expression of various constructs engineered in CD8 purified T cells and (12C) shows testing of the various variants for degranulation and cytokine production.
Figure 12B:
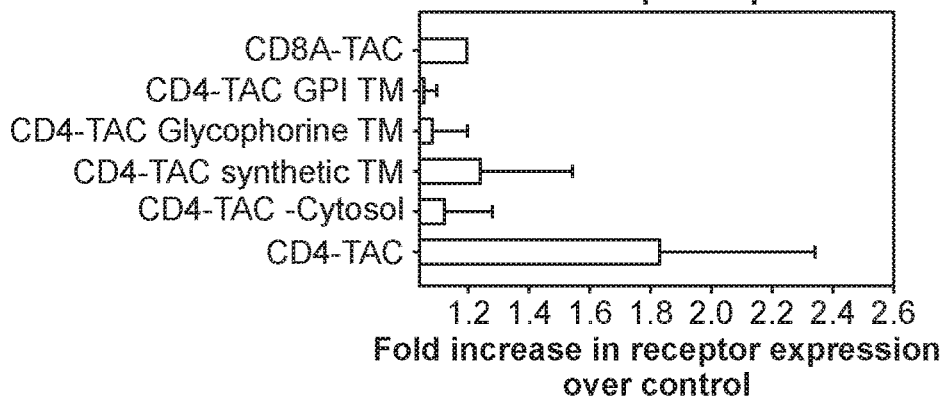
Figure 12C:
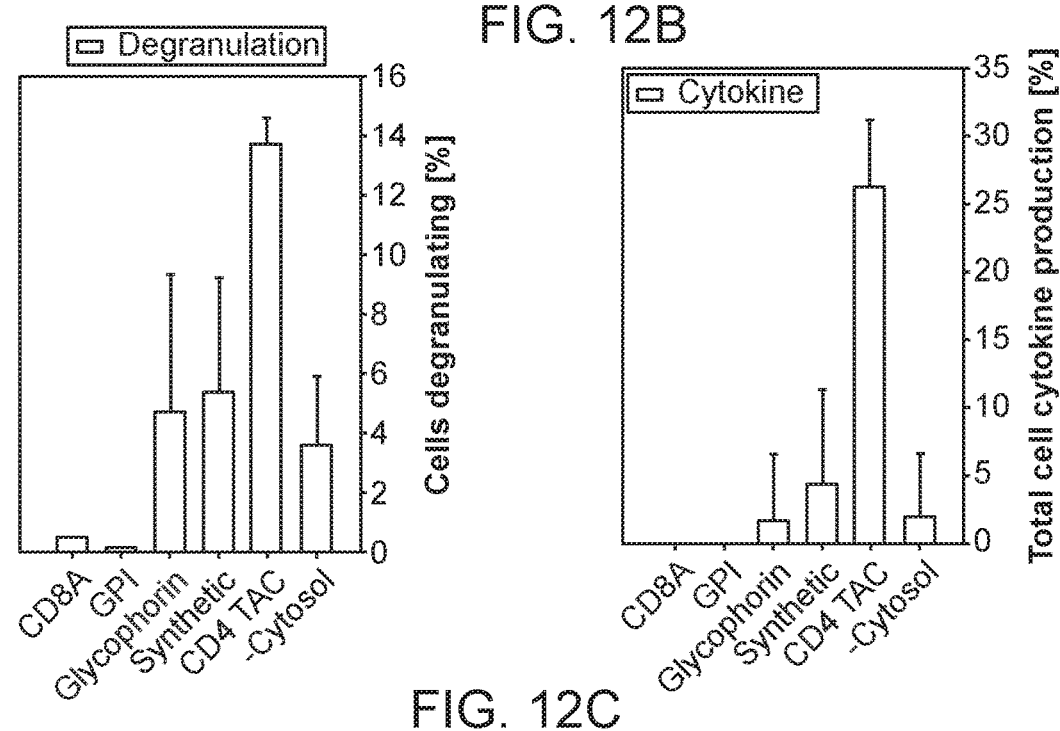

FIG. 12 shows properties of various transmembrane TAC variants. FIG. 12A is an overview of the various transmembrane constructs. The first set of variants is lacking the cytosolic domain. The CD4 TAC-cytosol has the entire cytosolic domain removed. The synthetic construct has the CD4 TM replaced by a designed, highly hydrophobic membrane domain. The glycophorine variant replaces the CD4 transmembrane domain with the glycophorine transmembrane domain. The GPI anchor variant uses the CD48 GPI signal sequenced to attach the TAC to the membrane using the GPI anchor. The CD8A TAC variant replaced the transmembrane and cytosolic CD4 domain with the CD8a counterpart. FIG. 12B shows CD8 purified T-cells were engineered with the various constructs. Surface expression of the various receptors relative to full length TAC is shown. All data is relative to the median fluorescent intensity of the control. All variants have a significantly lower receptor surface expression compared to the full length CD4-TAC. The GPI anchor TAC variant is not detectable above background. FIG. 12C depicts testing of the different variants for degranulation and cytokine production. Cells were incubated with plate pound Her2 antigen. The activity is presented as percent of cells positive for either the degranulation maker CD107a (left bar graph) or the percent of all cytokine producing cells taken together (TNFα, IFNg and TNFα/IFNg, right bar graph). GPI anchored or CD8a variants show background levels of degranulation and cytokine production. Glycophorine, synthetic and -cytosol TAC variants show a moderate level of degranulation and a low level of cytokine production. In all cases the activity is well below full length CD4-TAC. Taken together this shows that anchoring TAC without its cytosolic domain leads to functional receptors with diminished activity.

Figure 13:
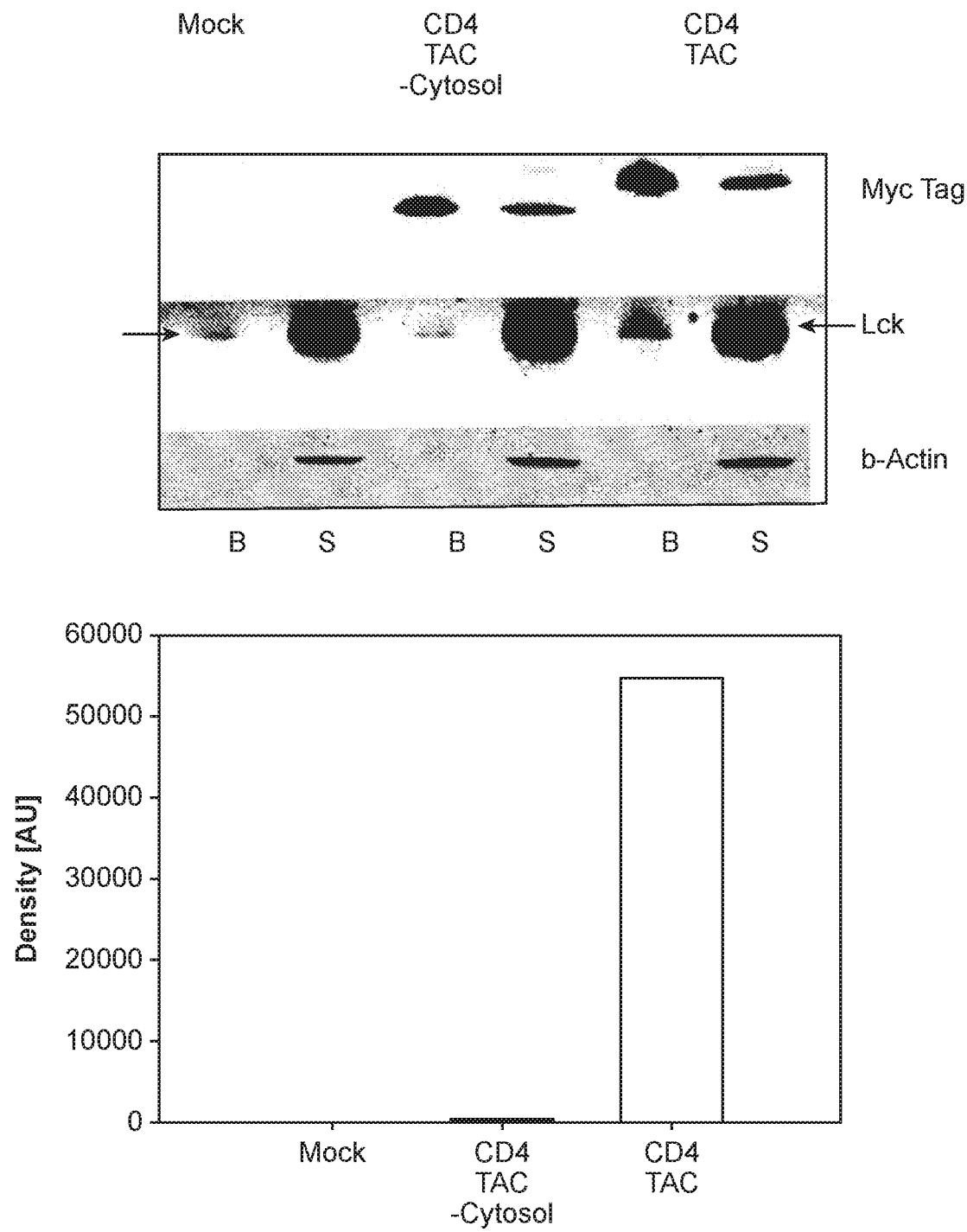

FIG. 13 shows Lck interaction with TAC variants. In FIG. 13A, Her2 antigen was covalently attached to magnetic beads. 293TM cells were engineered to express both the TAC and TAC cytosolic deletion variant as well as Lck. Beads were incubated with cell lysates over night and subsequently washed and western blotted. Lck was detected using an Lck antibody, TACs were detected via Myc antibody. B-Actin was used as control. b-Actin was not pulled down and only detected in the supernatant (S). However both full length TAC and cytosolic deletion were efficiently pulled down and detected in the pellet fraction (B). Vector control and TAC without cytosolic domain show comparable levels of background Lck signal. Full length CD4 TAC however shows a significant level of Lck relative to the total amount. FIG. 13B shows densitometry analysis of the Lck detected in the pellet. Signal was corrected relative to the negative control. This data supports that Lck is able to interact with full length CD4-TAC.

Figure 14A:
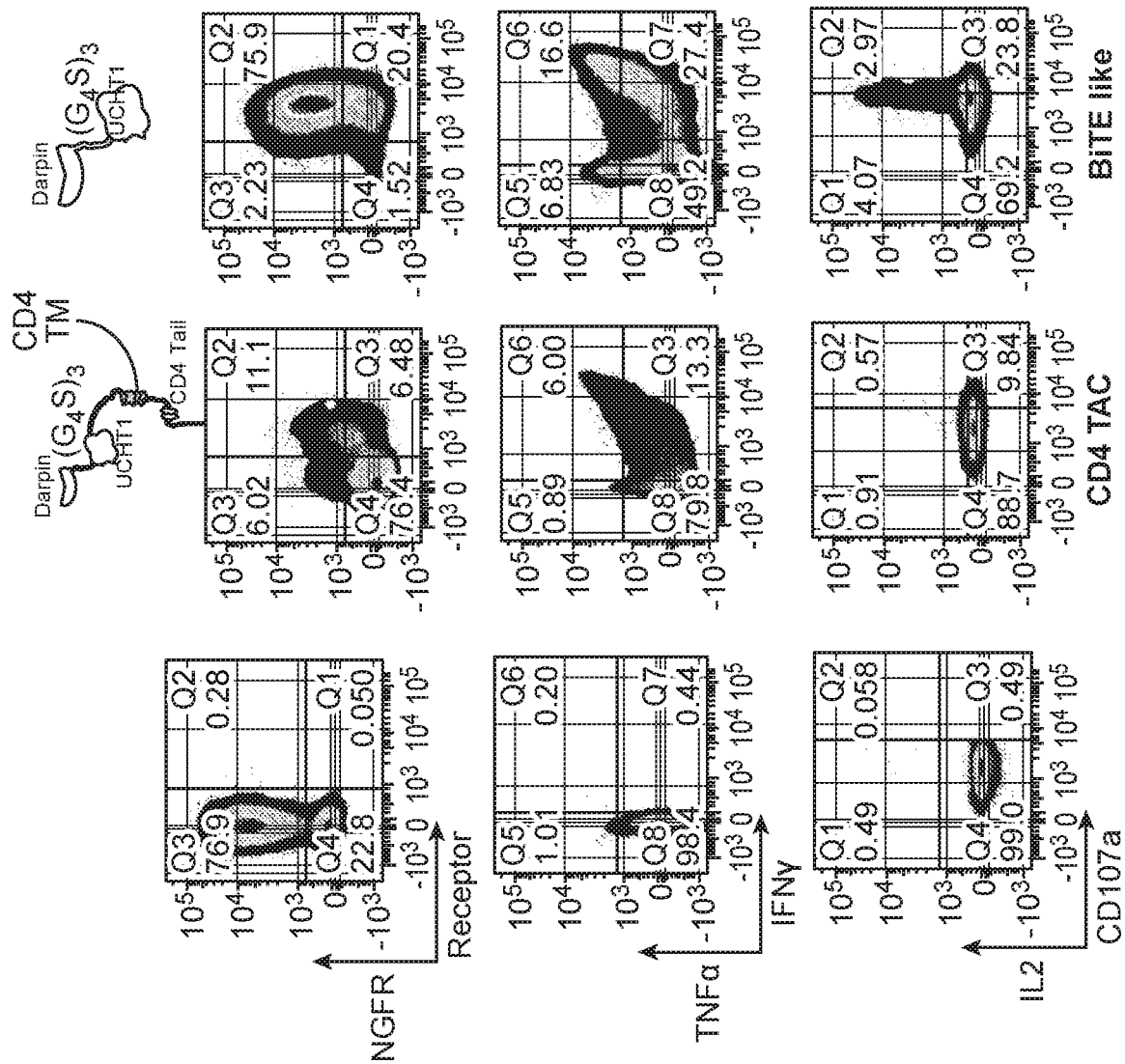
FIGS. 14A-B show CD4 TAC surface expression and activity compared to a BiTE like variant. (14A) depicts surface expression of an NGFR only control, CD4 TAC and BiTE like variant and (14B) compares cytotoxicity in various cell lines.
Figure 14B:
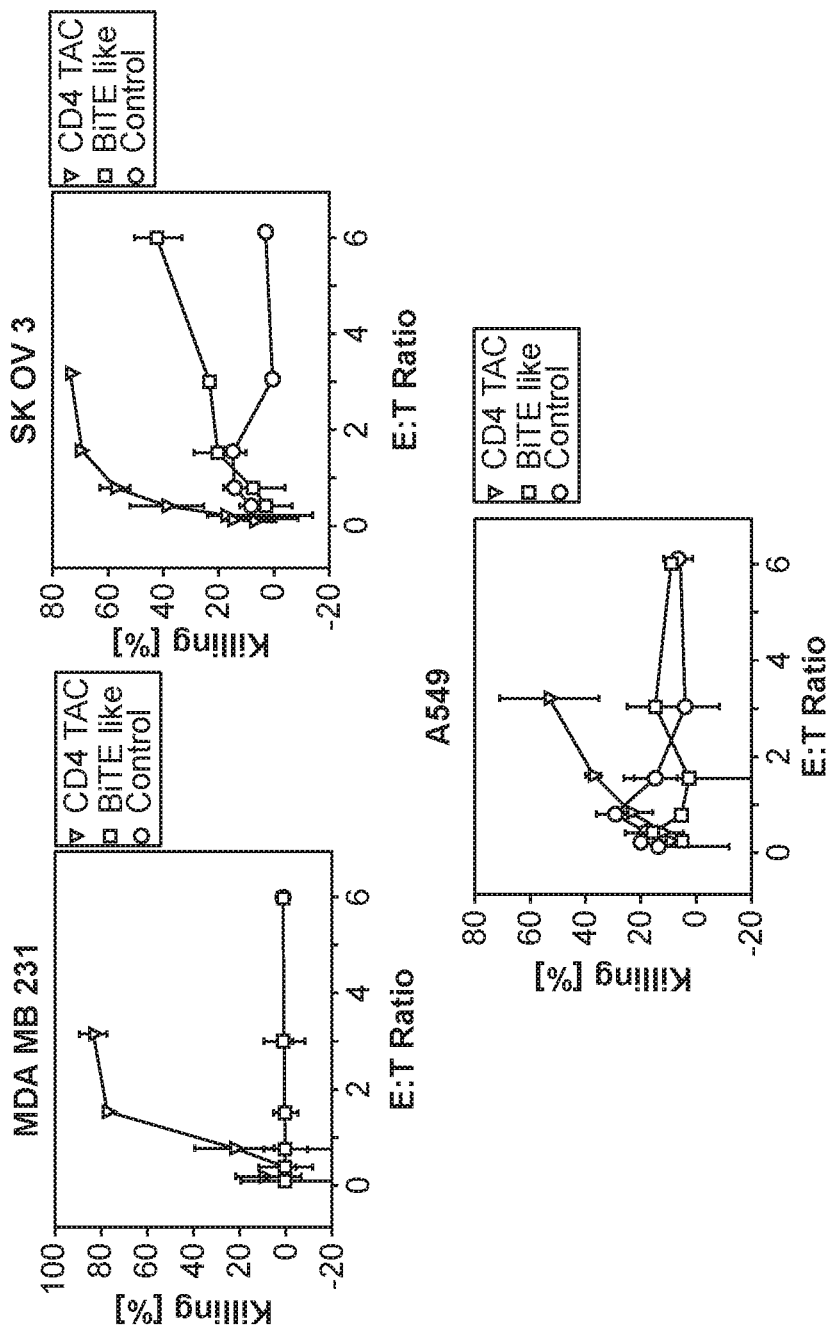

In FIG. 14, CD4 TAC surface expression and activity is compared to a BiTE like variant. FIG. 14A shows NGFR only control (left), CD4 TAC (middle) and BiTE like variant (right). Surface expression was tested using the transduction marker NGFR and the Her2 antigen. TAC shows much lower surface expression compared to BiTEs. Most notably, BiTE seems to secrete enough coupling antibody to enable transduction negative cells (NGFR-) to show strong receptor expression. Both cytokine production and degranulation are higher in BiTE like cells compared to TAG engineered cells. FIG. 14B compares cytotoxicity in various Her2 positive cell lines (MDA MB 231, SK OV 3, A549). In contrast to cytokine production, TAG engineered cells show significantly enhanced cytotoxic activity.

Figure 15C:
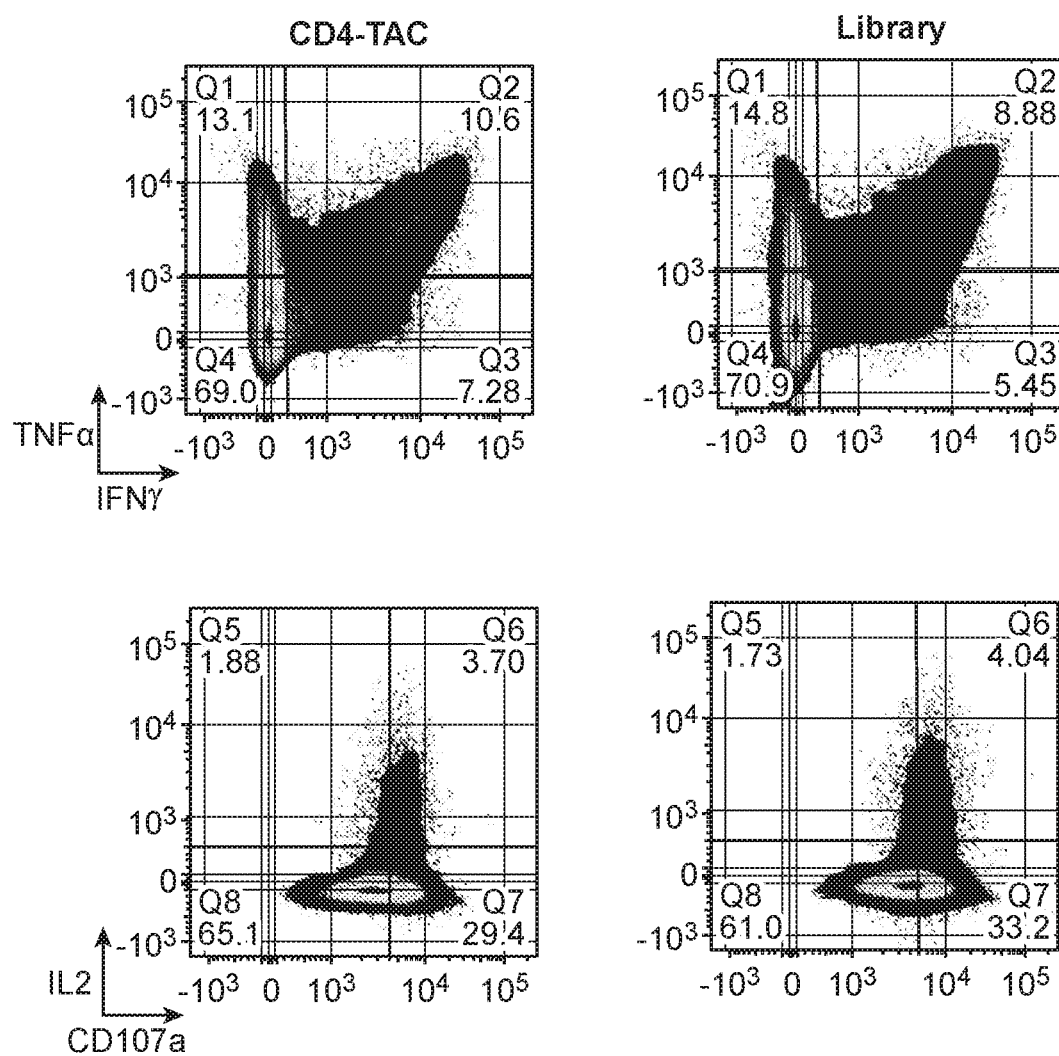

FIG. 15 shows comparison of CD4 TAG WT to a random mutagen library of UCHT1. To test the ability to change TAG properties, 24 amino acids found on the binding surface of UCHT1 and TCR epsilon were individually mutated. This gives rise to a theoretical number of 480 unique clones, all of which should be represented in this random library. FIG. 15A shows the schematic representation of the mutant. Markings indicate the mutations which are all in the scFv-epsilon interface. Figure FSB is a histogram of surface expression. Engineered cells were probed with FcHer2 antigen to detect surface expressed receptor. The library shows a much enhanced surface expression of the receptor. FIG. 15C shows WT and Library CD4 TAG cells incubated with plate bound antigen. Their ability to activate and produce cytokines is presented. The library has similar activity compared to the WT. Without being bound by theory, this supports the idea that expression properties of TAG can be improved while retaining the original functional profile by altering the scFv domain.

FIG. 16 shows enhanced surface expression of the A85V, T161P mutant. The library was propagated for an extended period of time to select for mutants with a growth advantage over the WT. A selected mutant was analysed (A85V, T161P; numbering is based on the UCHT1 domain fragment). FIG. 16A shows peripheral blood mononuclear cells (PBMC) were engineered with either WT CD4-TAC or the A85V, T161P mutant. The final CD4/CD8 populations between CD4 TAG (left) and A85V, T161P mutant (right) are compared. Notably, WT CD4-TAC leads to a reduced population of CD4 positive cells. This effect is not observed in the mutant cells. FIG. 16B shows surface expression, as determined by NGFR transduction maker and FcHer2 positivity, and indicates enhanced surface expression of the A85V, T161P mutant. FIG. 16C shows that A85V, T161P mutant cytokine production is diminished (DMSO controls showed no activity, data not shown). Degranulation between WT TAC and A85V, T161P mutant is comparable.

Figure 17A:
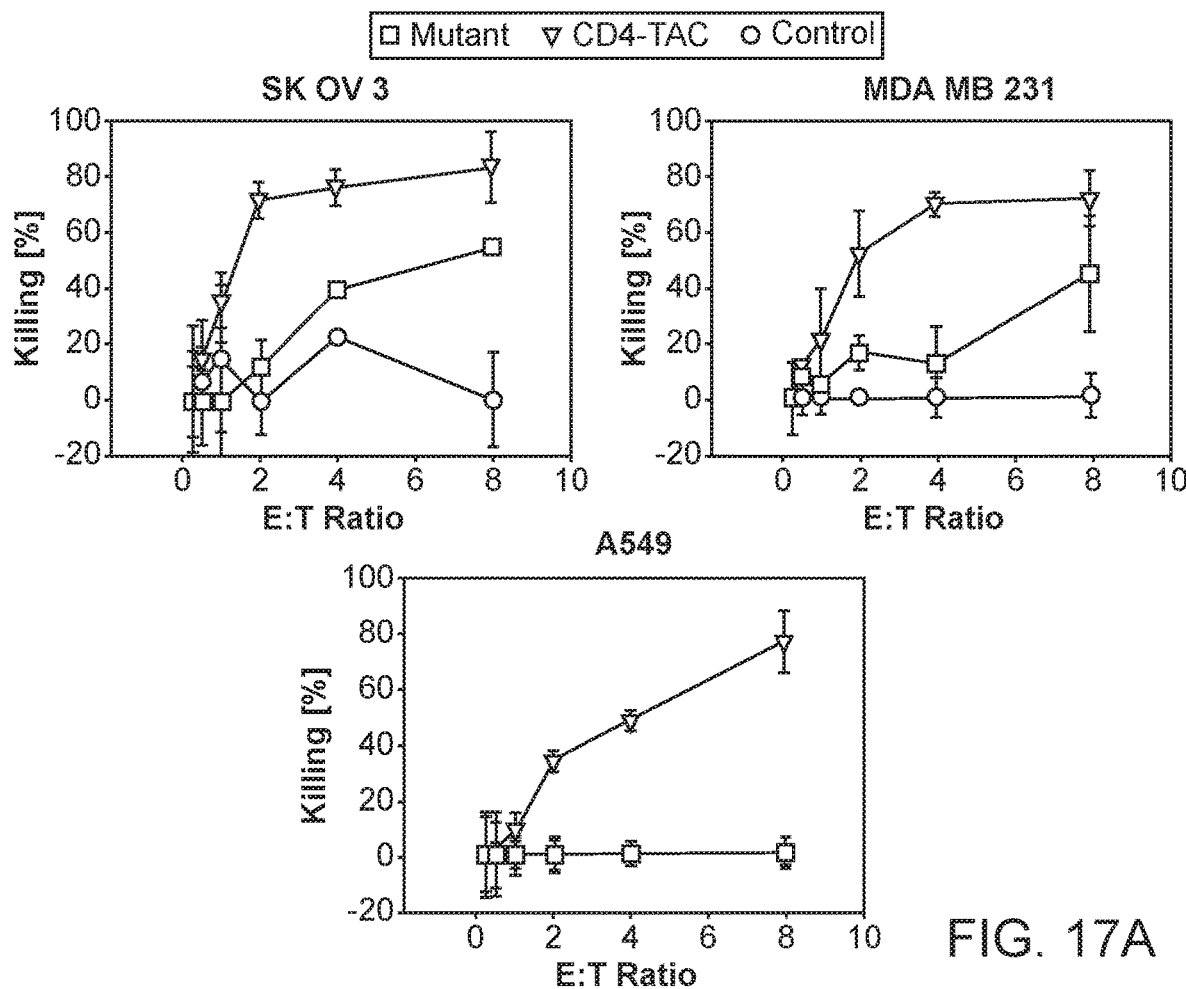
FIGS. 17A-B shows A85V, T161P mutant cytotoxicity and growth. (17A) shows cytotoxicity of the A85V, T161P mutant in various cell lines and (17B) shows cell growth in culture over 2 weeks.
Figure 17B:
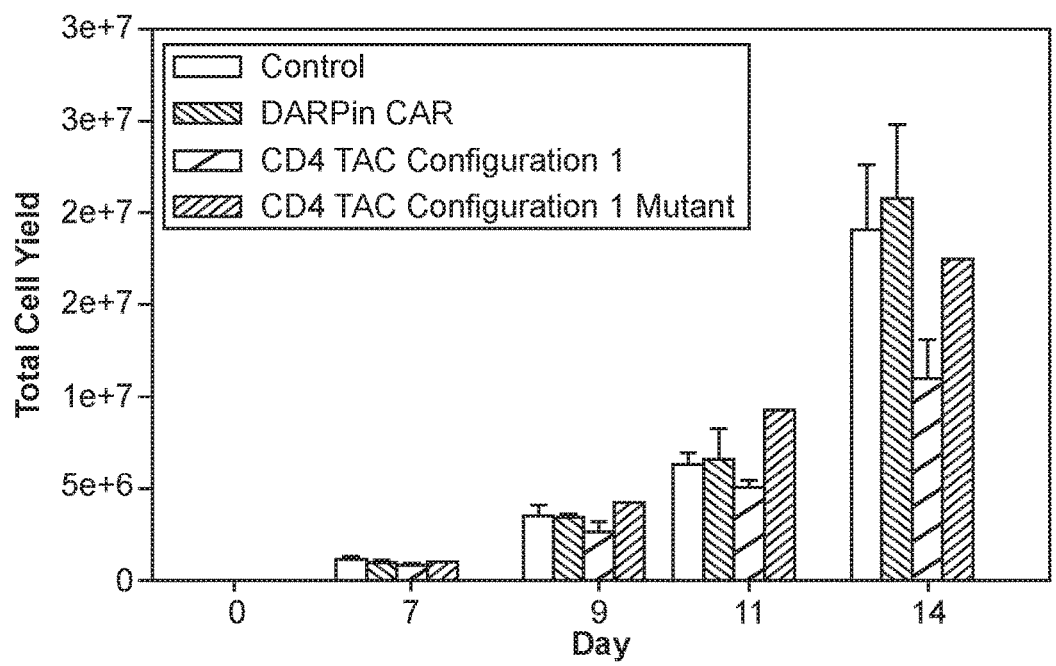

FIG. 17 shows A85V, T161P mutant cytotoxicity and growth. In FIG. 17A, T-cells engineered with WT CD4 TAC and A85V, T161P mutant were incubated with the Her2 antigen positive cell lines SK OV 3, MDA MB 231 and A549. In all cases, the mutant displayed a reduced level of cytotoxicity; in the case of A549, no cytotoxicity was detected. In FIG. 17B, cell growth in culture starting with 100 000 cells was monitored over 2 weeks. Periodically samples were taken and cells were counted manually. The A85V, T161P mutant exhibits markedly improved growth compared to the WT variant. Taken together, this demonstrates that the library is likely to contain various mutants that enable the modification and optimization of several TAC functions. Thus, UCHT1 can be used as a functional modulator.

While the present application has been described with reference to what are presently considered to be the preferred examples, it is to be understood that the application is not limited to the disclosed examples. To the contrary, the application is intended to cover various modifications and equivalent arrangements included within the spirit and scope of the appended claims.

All publications, patents, and patent applications are herein incorporated by reference in their entirety to the same extent as if each individual publication, patent or patent application was specifically and individually indicated to be incorporated by reference in its entirety.

REFERENCES

Acuto, O., and Cantrell, D. (2000). T cell activation and the cytoskeleton. Annu. Rev. Immunol. 18, 165-184.

Arcaro, a, Gregoire, C., Boucheron, N., Stotz, S., Palmer, E., Malissen, B., and Luescher, I. F. (2000). Essential role of CD8 palmitoylation in CD8 coreceptor function. J. Immunol. 165, 2068-2076.

Chames, P., and Baty, D. (2009). Bispecific antibodies for cancer therapy: the light at the end of the tunnel? MAbs 1, 539-547.

Chervin, A. S., Stone, J. D., Holler, P. D., Bai, A., Chen, J., Eisen, H. N., and Kranz, D. M. (2009). The impact of TCR-binding properties and antigen presentation format on T cell responsiveness. J. Immunol. 183, 1166-1178.

Dotti, G., Savoldo, B., and Brenner, M. (2009). Fifteen years of gene therapy based on chimeric antigen receptors: "are we nearly there yet?". Hum. Gene Ther. 20, 1229-1239.

Finney, H. M., Akbar, A. N., and Lawson, A. D. G. (2004). Activation of resting human primary T cells with chimeric receptors: costimulation from CD28, inducible costimulator, CD134, and CD137 in series with signals from the TCR zeta chain. J. Immunol. 172, 104-113.

Fragoso, R., Ren, D., Zhang, X., Su, M. W.-C., Burakoff, S. J., and Jin, Y.-J. (2003). Lipid raft distribution of CD4 depends on its palmitoylation and association with Lck, and evidence for CD4-induced lipid raft aggregation as an additional mechanism to enhance CD3 signaling. J. Immunol. 170, 913-921.

Fry, T. J., and Mackall, C. L. (2013). T-cell adoptive immunotherapy for acute lymphoblastic leukemia. Hematology Am. Soc. Hematol. Educ. Program 2013, 348-353.

Han, E. Q., Li, X., Wang, C., Li, T., and Han, S. (2013). Chimeric antigen receptor-engineered T cells for cancer immunotherapy: progress and challenges. J. Hematol. Oncol. 6, 47.

He, H.-T., and Marguet, D. (2008). T-cell antigen receptor triggering and lipid rafts: a matter of space and time scales. Talking Point on the involvement of lipid rafts in T-cell activation. EMBO Rep. 9, 525-530.

Humphries, C. (2013). Adoptive cell therapy: Honing that killer instinct. Nature 504, 313-5.

Kim, P. W., Sun, Z. J., Blacklow, S. C., Wagner, G., and Eck, M. J. (2003). A zinc clasp structure tethers Lck to T cell coreceptors CD4 and CD8. Science 301, 1725-1728.

Kochenderfer, J. N., and Rosenberg, S. A. (2013). Treating B-cell cancer with T cells expressing anti-CD19 chimeric antigen receptors. Nat. Rev. Clin. Oncol. 10, 267-276.

Kuhns, M. S., and Davis, M. M. (2012). TCR Signaling Emerges from the Sum of Many Parts. Front. Immunol. 3, 159.

Methi, T., Ngai, J., Mahic, M., Amarzguioui, M., Vang, T., and Tasken, K. (2005). Short-interfering RNA-mediated Lck knockdown results in augmented downstream T cell responses. J. Immunol. 175, 7398-7406.

Milone, M. C., Fish, J. D., Carpenito, C., Carroll, R. G., Binder, G. K., Teachey, D., Samanta, M., Lakhal, M., Gloss, B., Danet-Desnoyers, G., et al. (2009). Chimeric receptors containing CD137 signal transduction domains mediate enhanced survival of T cells and increased anti-leukemic efficacy in vivo. Mol. Ther. 17, 1453-1464.

Portell, C. a, Wenzell, C. M., and Advani, A. S. (2013). Clinical and pharmacologic aspects of blinatumomab in the treatment of B-cell acute lymphoblastic leukemia. Clin. Pharmacol. 5, 5-11.

Yin, Y., Wang, X. X., and Mariuzza, R. a (2012). Crystal structure of a complete ternary complex of T-cell

SEQUENCE LISTING

The instant application contains a Sequence Listing which has been submitted electronically in ASCII format and is hereby incorporated by reference in its entirety. Said ASCII copy, created on Aug. 21, 2019, is named 55247702301_SL.txt and is 30,993 bytes in size.

The invention claimed is:

1. A B-cell maturation antigen (BCMA) T cell Antigen Coupler (BCMA-TAC), comprising: a) a first antigen binding domain polypeptide which binds BCMA; b) a second antigen binding domain polypeptide that binds a CD3 epsilon protein associated with a TCR complex on the T cell; and c) a T cell co-receptor domain polypeptide comprising a CD4 cytosolic domain and a CD4 transmembrane domain; wherein the components (a), (b) and (c) are fused directly to each other or joined by at least one linker, and provided that the BCMA-TAC does not comprise a co-stimulatory domain.

2. The BCMA-TAC of claim 1, wherein the first antigen binding domain polypeptide is a scFv.

3. The BCMA-TAC of claim 1, wherein the second antigen binding domain polypeptide comprises an amino acid sequence having at least 99% identity to the amino acid sequence as set forth in SEQ ID NO: 14.

4. The BCMA-TAC of claim 1, wherein the second antigen binding domain polypeptide comprises the amino acid sequence as set forth in SEQ ID NO: 14.

5. The BCMA-TAC of claim 1, wherein the T cell co-receptor domain polypeptide comprises an amino acid sequence having at least 99% identity to the amino acid sequence as set forth in SEQ ID NO: 18.

6. The BCMA-TAC of claim 1, wherein the T cell co-receptor domain polypeptide comprises the amino acid sequence as set forth in SEQ ID NO: 18.

7. A T cell expressing a BCMA-TAC according to claim 1.

8. A pharmaceutical composition, comprising the T cell of claim 7, and a carrier.

9. A method of treating a BCMA-expressing cancer in an individual in need thereof, the method comprising administering the pharmaceutical composition of claim 8 to the individual, thereby treating the BCMA-expressing cancer.

* * * * *